United States Patent
Maltz et al.

(10) Patent No.: US 7,486,773 B2
(45) Date of Patent: Feb. 3, 2009

(54) MEGAVOLTAGE SCATTER RADIATION MEASUREMENT USING BEAM STOP ARRAY

(75) Inventors: Jonathan S. Maltz, Oakland, CA (US); Zirao Zheng, Petaluma, CA (US); Michelle M. Svatos, Oakland, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 308 days.

(21) Appl. No.: 11/431,490

(22) Filed: May 9, 2006

(65) Prior Publication Data

US 2008/0067386 A1 Mar. 20, 2008

(51) Int. Cl.
G01B 15/02 (2006.01)
G01N 23/20 (2006.01)
G01N 23/201 (2006.01)
H01L 27/146 (2006.01)
H01J 37/295 (2006.01)

(52) U.S. Cl. .................. 378/90; 378/6; 378/7; 378/70; 378/86; 378/87; 378/98.11; 378/98.12; 250/358.1; 250/370.08; 250/370.09

(58) Field of Classification Search .............. 250/358.1, 250/363.01, 363.05, 367–369, 370.08, 370.09, 250/370.1, 493.1; 378/1, 4, 6, 7, 10, 20, 378/21, 22, 29, 55, 62, 70, 86, 87, 90, 98.11, 378/98.12, 98.8
See application file for complete search history.

(56) References Cited

U.S. PATENT DOCUMENTS

| | | | | |
|---|---|---|---|---|
| 4,549,307 | A | | 10/1985 | Macovski |
| 4,727,562 | A | * | 2/1988 | Belanger .................... 378/98.4 |
| 5,376,795 | A | * | 12/1994 | Hasegawa et al. ....... 250/363.04 |
| 5,572,034 | A | * | 11/1996 | Karellas ...................... 250/368 |
| 5,648,997 | A | * | 7/1997 | Chao .......................... 378/98.4 |
| 6,865,254 | B2 | * | 3/2005 | Nafstadius .................... 378/65 |
| 6,980,626 | B2 | * | 12/2005 | Groh et al. ..................... 378/87 |
| 7,046,757 | B1 | * | 5/2006 | Bani-Hashemi et al. ........ 378/7 |
| 2004/0079232 | A1 | * | 4/2004 | Groh et al. ........................ 96/1 |
| 2004/0096033 | A1 | * | 5/2004 | Seppi et al. .................... 378/65 |
| 2006/0264755 | A1 | * | 11/2006 | Maltz et al. .................. 600/455 |
| 2007/0086560 | A1 | * | 4/2007 | Kia et al. ......................... 378/7 |
| 2008/0049892 | A1 | * | 2/2008 | Maltz ........................... 378/19 |
| 2008/0067386 | A1 | * | 3/2008 | Maltz et al. .................. 250/311 |

FOREIGN PATENT DOCUMENTS

EP 0 689 047 B1 9/1998

OTHER PUBLICATIONS

Ruola Ning, Xiangyang Tang and David Conover, X-ray scatter correction algorithm for cone beam CT imaging, Medical Physics, vol. 31 No. 5, May 2004, pp. 1195-1202. © 2004 Am. Assoc. Phys. Med.

* cited by examiner

Primary Examiner—Bernard E Souw

(57) ABSTRACT

A system may include emission of megavoltage radiation from a megavoltage radiation source, acquisition of a first image using an imaging device while first megavoltage radiation is emitted from the megavoltage radiation source and while a plurality of elements is between the megavoltage radiation source and the imaging device, and determination of an amount of scatter radiation based at least on areas of the acquired image corresponding to the plurality of elements. In some aspects, at least one of the plurality of elements is substantially pointed toward a focal spot of the megavoltage radiation source.

22 Claims, 20 Drawing Sheets

MEGAVOLTAGE SCATTER RADIATION MEASUREMENT USING BEAM STOP ARRAY

BACKGROUND

1. Field

The embodiments described herein relate generally to systems for generating megavoltage radiation. More particularly, the described embodiments relate to the determination of megavoltage scatter radiation using one or more radiation-attenuating elements.

2. Description

A linear accelerator produces electrons or photons having particular energies. In one common application, a linear accelerator generates a radiation beam exhibiting megavoltage energies and directs the beam toward a target area of a patient. The beam is intended to destroy cells within the target area by causing ionizations within the cells or other radiation-induced cell damage.

Radiation treatment plans are intended to maximize radiation delivered to a target while minimizing radiation delivered to healthy tissue. A radiation treatment plan designer must assume that relevant portions of a patient will be in particular positions relative to a linear accelerator during delivery of the treatment radiation. The goals of maximizing target radiation and minimizing healthy tissue radiation may not be achieved if the relevant portions are not positioned in accordance with the treatment plan during delivery of the radiation. More specifically, errors in positioning the patient can cause the delivery of low radiation doses to tumors and high radiation doses to sensitive healthy tissue. The potential for misdelivery increases with increased positioning errors.

Imaging systems may be used to verify patient positioning prior to the delivery of treatment radiation. According to some examples, a radiation beam is emitted by a linear accelerator prior to treatment, passes through a volume of the patient and is received by an imaging system. The imaging system produces a set of data that represents the attenuative properties of objects of the patient volume that lie between the radiation source and the imaging system.

The set of data is used to generate a two-dimensional portal image of the patient volume. The portal image will include areas of different intensities that reflect different compositions of the objects. For example, areas of low radiation intensity may represent bone and areas of high radiation intensity may represent tissue. Several two-dimensional portal images may be acquired from different perspectives with respect to the patient volume and combined to generate a three-dimensional image of the patient volume. The foregoing images may be used to diagnose illness, to plan radiation therapy, to confirm patient positioning prior to therapy, and/or to confirm a shape and intensity distribution of a radiation field prior to therapy.

The imaging system receives scatter radiation during acquisition of the above-described portal images. Such scatter radiation does not travel along an expected radiation trajectory from the radiation source to the imaging system. In other words, scatter radiation received at a particular location of the imaging system does not reflect attenuative properties of all the tissues located along an expected trajectory from the radiation source to the particular location. As a result, received scatter radiation induces noise and reduces the intensity gradients (i.e. contrast) between image areas that represent different objects in a portal image. The reduced contrast may inhibit identification of structures within the portal image, particularly with respect to soft tissue structures.

Conventional single-row (one-dimensional) imaging systems include a row of radiation detectors to detect kilovoltage radiation. These systems may include thin metal collimators to prevent scatter radiation from reaching the radiation detectors. Such techniques are impractical for two-dimensional imaging systems employing thousands of detectors. The techniques are particularly impractical for megavoltage radiation-based imaging due to the collimator masses that would be required to block megavoltage scatter radiation.

Some conventional kilovoltage radiation-based imaging systems determine scatter radiation by acquiring a first image of an object with an imaging device while an array of dense cylindrical elements lies between a kilovoltage radiation source and the object. The elements prevent primary photons from the radiation source from reaching the imaging device and therefore produce shadows within the first image. The shadows are assumed to be uniformly absent of non-scatter radiation and any photon fluence detected in the shadows is therefore assumed to have undergone scatter. Scatter radiation may therefore be measured based on fluence within the shadows and the foregoing assumptions.

The above-described approach is not suitable for high-energy systems. For example, the cylindrical elements used in conventional kilovoltage radiation-based imaging systems would not sufficiently or uniformly attenuate photons of a megavoltage radiation beam. Accordingly, the aforementioned assumptions would not be valid and any measurements of scatter radiation based on such assumptions would be unsuitably inaccurate.

It would therefore be beneficial to provide an efficient system to determine an amount of scatter radiation resulting from irradiation of an object with megavoltage radiation. Such a determination may facilitate efficient reduction of scatter-induced noise within an image of the object.

SUMMARY

In order to address the foregoing, some embodiments provide a system, method, apparatus, and means to place a plurality of elements between a megavoltage radiation source and an imaging device, emit megavoltage radiation from the megavoltage radiation source, acquire a first image while first megavoltage radiation is emitted from the megavoltage radiation source and while the plurality of elements is between the megavoltage radiation source and the imaging device, and determine an amount of scatter radiation based at least on areas of the acquired image corresponding to the plurality of elements.

In some aspects, at least one of the plurality of elements is substantially pointed toward a focal spot of the megavoltage radiation source. The emitted radiation follows a divergent path, and an outer surface of at least one of the plurality of elements is substantially aligned with the divergent path according to some aspects.

Further aspects also may include acquisition of a second image while second megavoltage radiation is emitted from the megavoltage radiation source and while the plurality of elements and an object to be imaged are not between the megavoltage radiation source and the imaging device, acquisition of a third image while third megavoltage radiation is emitted from the megavoltage radiation source, and while the plurality of elements and the object to be imaged are between the megavoltage radiation source and the imaging device, and acquisition of a fourth image while fourth megavoltage radiation is emitted from the megavoltage radiation source, while the object is between the megavoltage radiation source and the imaging device, and while the plurality of elements is not between the megavoltage radiation source and the imaging device.

Further to the foregoing aspect, determination of the amount of scatter radiation may include determining, for each of the corresponding areas, an amount of scatter radiation due to the object based on the first image, the second image, the third image, and the fourth image, wherein the object to be imaged is not between the megavoltage radiation source and the imaging device during acquisition of the first image.

The appended claims are not limited to the disclosed embodiments, however, as those in the art can readily adapt the descriptions herein to create other embodiments and applications.

BRIEF DESCRIPTION OF THE DRAWINGS

Embodiments will become readily apparent from consideration of the following specification as illustrated in the accompanying drawings, in which like reference numerals designate like parts, and wherein.

DETAILED DESCRIPTION

The following description is provided to enable a person in the art to make and use some embodiments and sets forth the best mode contemplated by the inventors for carrying out some embodiments. Various modifications, however, will remain readily apparent to those in the art.

Figure 1:
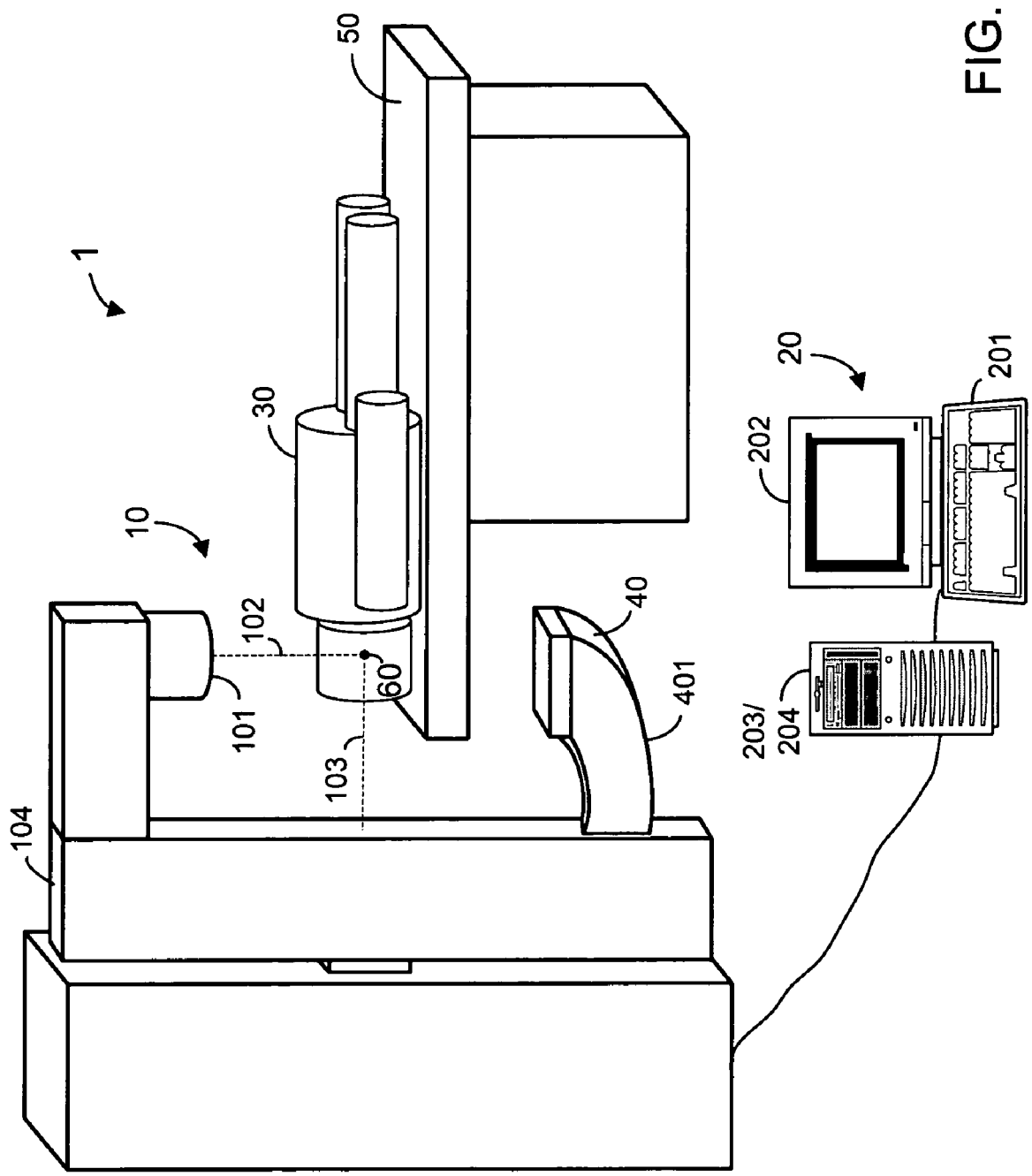
FIG. 1 is a perspective view of a linear accelerator system according to some embodiments.

FIG. 1 is a perspective view of system 1 according to some embodiments. Shown are linear accelerator 10, operator console 20, beam object 30, imaging device 40 and table 50. System 1 may be used to generate high-energy radiation for imaging and/or for medical radiation treatment. In this regard, beam object 30 comprises a patient positioned to receive treatment radiation according to a radiation treatment plan. System 1 may be employed in other applications according to some embodiments.

In one operational example according to some embodiments, an array of elements are placed between linear accelerator 10 and imaging device 40, linear accelerator 10 emits megavoltage radiation, imaging device 40 acquires a first image while first megavoltage radiation is emitted from linear accelerator 10 and while the array of elements is between linear accelerator 10 and imaging device 40, and operator console 20 determines an amount of scatter radiation based at least on areas of the acquired image corresponding to the array of elements. The foregoing features may provide efficient determination of scatter radiation due to object 30. Moreover, the determined amount of scatter radiation may be used to reduce scatter-induced noise within an image of object 30 acquired by imaging device 40.

Dealing with each illustrated system in turn, linear accelerator 10 generally delivers a high-energy (e.g., megavoltage) radiation beam from treatment head 101 toward a volume of object 30 at isocenter 60. Isocenter 60 may be located at an intersection of axis 102 of the aforementioned radiation beam and axis 103 around which gantry 104 is rotatable. According to some embodiments, the radiation beam may comprise photon or electron radiation.

Treatment head 101 includes a beam-emitting device (not shown) for emitting the radiation beam. Also included within treatment head 101 may be a beam-shielding device, or collimator, for shaping the beam and for shielding sensitive surfaces from the beam. Due to characteristic divergence of the radiation beam and the aforementioned shaping of the beam, the radiation beam delivers radiation to a radiation field rather than only to isocenter 60. An accessory tray may be mounted on treatment head 101 and configured to receive and securely hold attachments used during the course of treatment planning and treatment. These attachments may include an array of beam-attenuating elements, reticles, wedges, filters and/or apertures.

Imaging device 40 may comprise any system to acquire an image based on received photon radiation (i.e., X-rays) and/or electron radiation. Imaging device 40 acquires images that are used before, during and after radiation treatment. For example, imaging device 40 may be used to acquire images for diagnosis, verification and recordation of a patient position, and verification and recordation of an internal patient portal to which treatment radiation is delivered. As described above, the effectiveness of radiation treatment often depends on the quality of the acquired images.

In operation, the scintillator layer receives X-rays and generates light in proportion to the intensity of the received X-rays. The array of photodiodes receives the light and records the intensity of received light as stored electrical charge. The stored charge therefore comprises an acquired image that represents intensities at each location of a radiation field produced by radiation beam 13. The bounds of the radiation field are determined by the physical intersection of the radiation beam with the surface of the scintillator layer.

In some embodiments, imaging device 40 is a flat-panel imaging device using a scintillator layer and solid-state amorphous silicon photodiodes deployed in a two-dimensional array. In other embodiments, imaging device 40 converts X-rays to electrical charge without requiring a scintillator layer. In such imaging devices, X-rays are absorbed directly by an array of amorphous selenium photoconductors. The photoconductors convert the X-rays directly to stored electrical charge that comprises an acquired image of a radiation field. Imaging device 40 may also comprise a CCD or tube-based camera. Such an imaging device may include a light-proof housing within which are disposed a scintillator, a mirror, and a camera.

Imaging device 40 may be attached to gantry 104 in any manner, including via extendible and retractable housing 401. Rotation of gantry 104 may cause treatment head 101 and imaging device 40 to rotate around the isocenter such that isocenter 60 remains located between treatment head 101 and imaging device 40 during the rotation.

Table 50 supports object 30 during image acquisition and/or radiation therapy. Table 50 is adjustable to ensure, along with rotation of gantry 104, that a volume of interest is positioned between treatment head 101 and imaging device 40. Table 50 may also be used to support devices used for acquisition of correction images, other calibration tasks and/or beam verification.

Operator console 20 includes input device 201 for receiving instructions from an operator such as an instruction to acquire a scatter-corrected image and an instruction to deliver treatment radiation according to a treatment plan. Console 20 also includes output device 202, which may be a monitor for presenting operational parameters of linear accelerator 10 and/or interfaces for controlling systems 10, 40 and/or 50. Output device 202 may also present images acquired by imaging device 40 during determination of an amount of scatter radiation and/or the above-mentioned scatter-corrected image. Input device 201 and output device 204 are coupled to processor 203 and storage 204.

Processor 203 executes program code according to some embodiments. The program code may be executable to control system 1 to operate as described herein. The program code may be stored in storage 204, which may comprise one or more storage media of identical or different types, including but not limited to a fixed disk, a floppy disk, a CD-ROM, a DVD-ROM, a Zip™ disk, a magnetic tape, and a signal. Storage 204 may, for example, store radiation treatment plans, portal images, software applications to calibrate system 1 and/or to provide radiation treatment, and other data used to perform radiation treatment.

Operator console 20 may be located apart from linear accelerator 10, such as in a different room, in order to protect its operator from radiation. For example, accelerator 10 may be located in a heavily shielded room, such as a concrete vault, which shields the operator from radiation generated by accelerator 10.

Each of the devices shown in FIG. 1 may include less or more components than those shown. In addition, embodiments are not limited to the components shown in FIG. 1.

Figure 2:
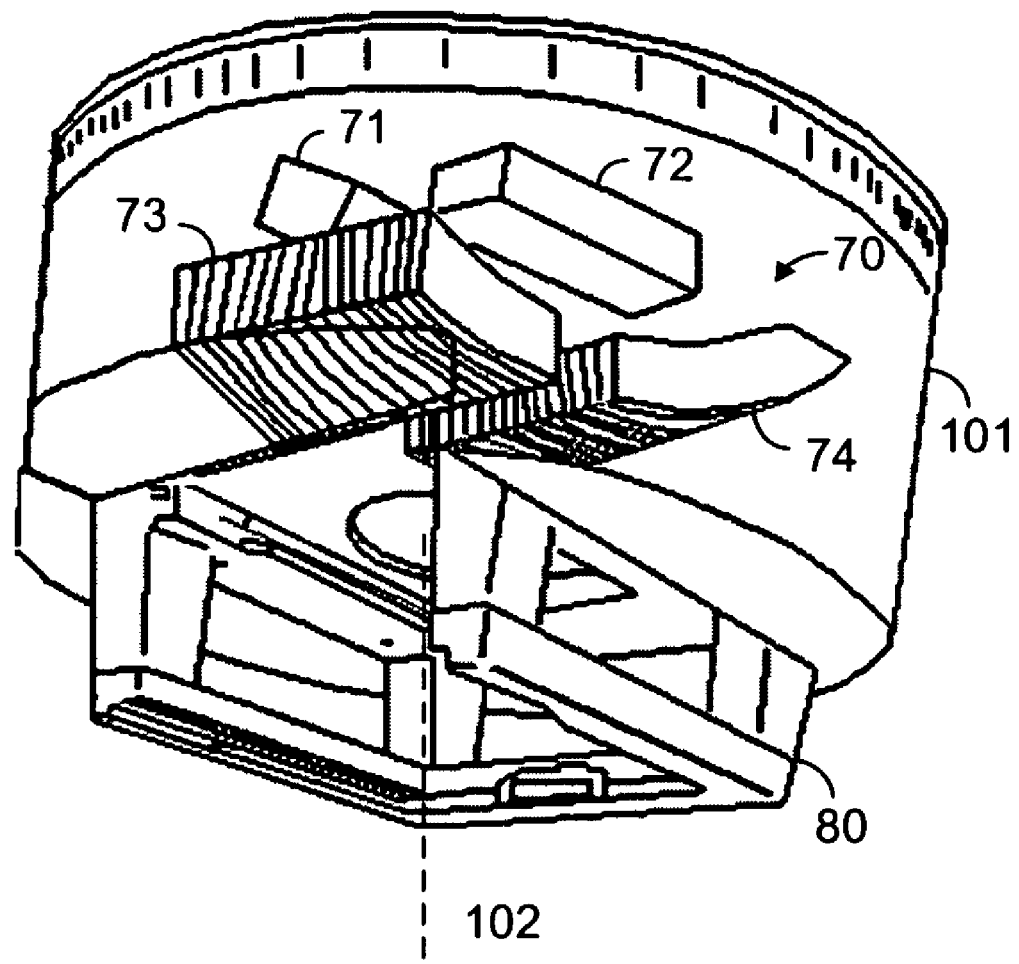
FIG. 2 is a transparent view of a treatment head including a multi-leaf collimator according to some embodiments.

FIG. 2 is a transparent view of treatment head 101 according to some embodiments. Treatment head 101 includes multi-leaf collimator 70 that may be used to shape a radiation beam. Collimator 70 includes a pair of jaws (Y-jaws) 71 and 72 and a pair of jaws (X-jaws) 73 and 74 generally disposed perpendicular to jaws 71 and 72. As depicted in FIG. 2, X-jaws 73 and 74 may be formed of a plurality of individual collimator "leaves". Each of these leaves may be independently movable along a path intersecting axis 102.

The positioning of Y-jaws 71 and 72 and the leaves of X-jaws 73 and 74 determines a size and shape of an opening through which a radiation beam may pass along axis 102. Each of X-jaws 73 and 74 and Y-jaws 71 and 72 are formed of radiation attenuating material. In one embodiment, the jaws are formed of material that has x-ray transmission characteristics of less than 1%, including but not limited to tungsten.

Treatment head 101 also includes accessory tray 80. Accessory tray 80 may be configured as described above to receive and securely hold attachments including but not limited to an array of beam-attenuating elements, reticles, wedges, filters and apertures. According to some embodiments, treatment head 101 is rotatable to rotate collimator 70 and accessory tray 80 around axis 102 while maintaining the physical relationships between X-jaws 73 and 74, Y-jaws 71 and 72, and accessory tray 80. In addition, one or both of X-jaws 73 and 74, and Y-jaws 71 and 72 may be rotatable independent from rotation of treatment head 101.

Figure 3:
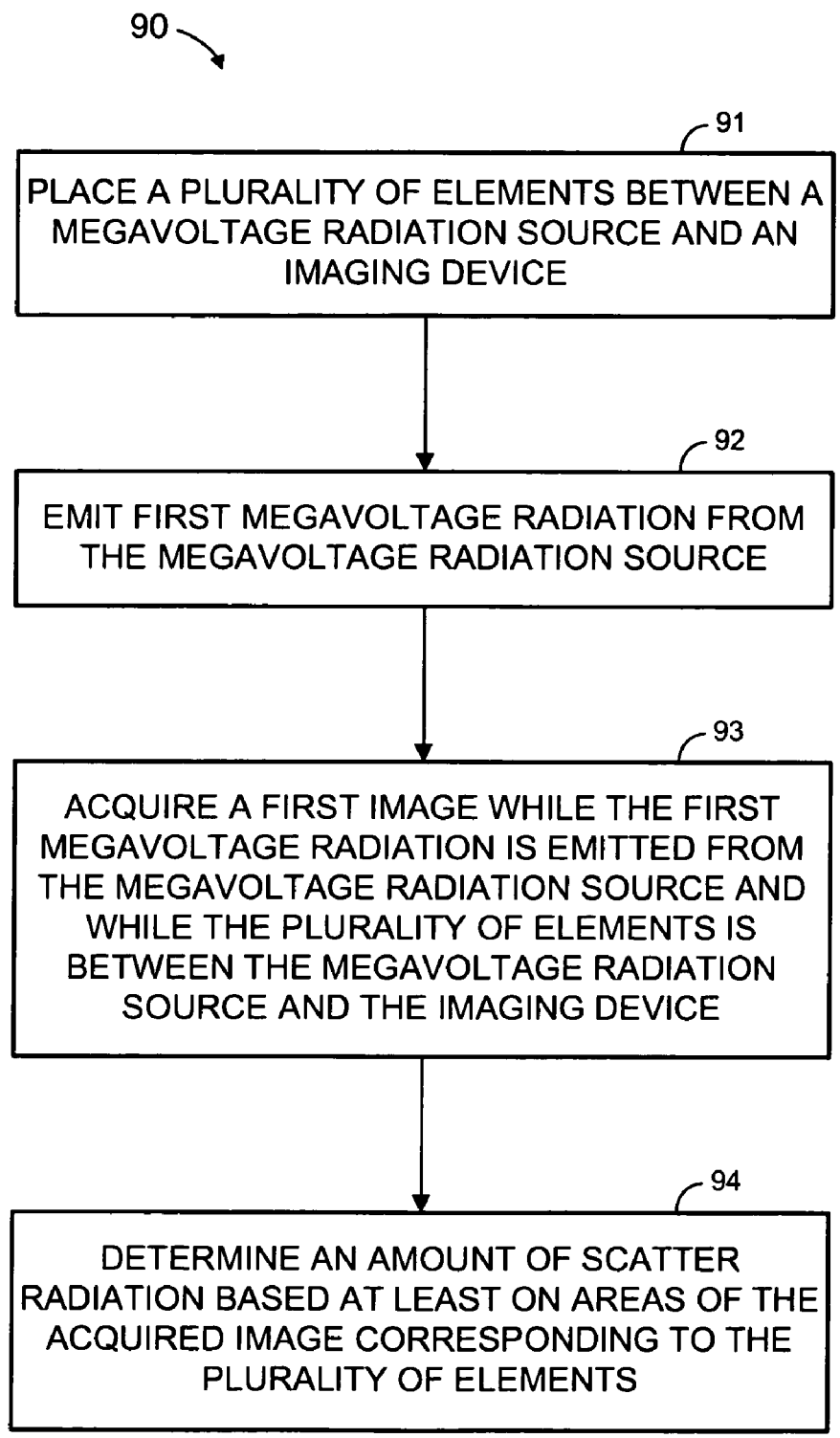
FIG. 3 is a flow diagram of process steps pursuant to some embodiments.

FIG. 3 is a flow diagram of process steps 90 according to some embodiments. Process steps 90 and all other process steps described herein may be executed by one or more components of linear accelerator 10, operator console 20, treatment head 101, imaging device 40, and other systems. Accordingly, these process steps may be embodied in hardware and/or software and, although described herein with respect to specific systems, may be implemented and executed differently than as described.

Prior to step 91, an operator may use input device 201 of operator console 20 to initiate operation of system 1. In response, processor 203 may execute program code of a system control application stored in storage 204. The operator may then operate input device 201 to initiate imaging of an object.

Figure 4A:
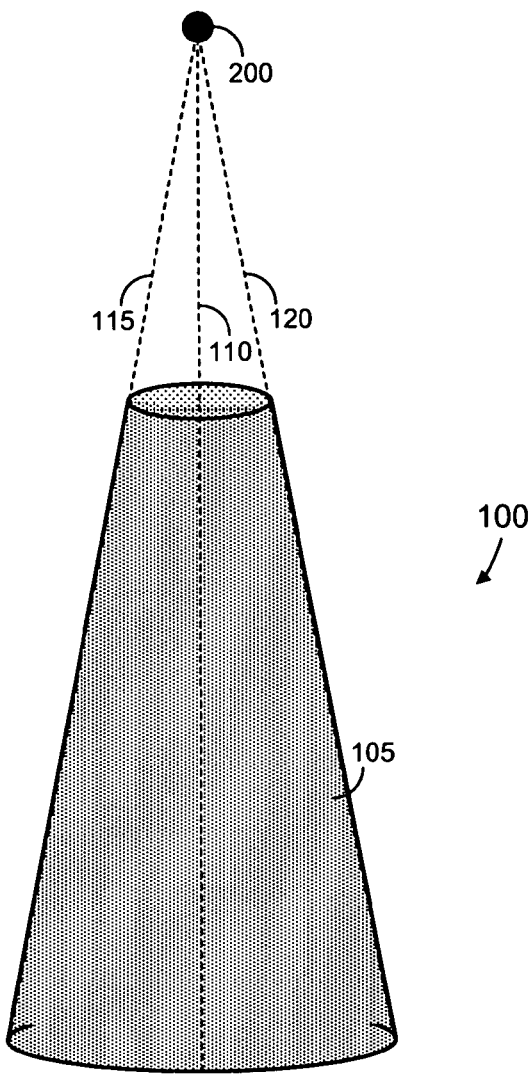
FIGS. 4A and 4B comprise side and top perspective views of a beam-attenuating element according to some embodiments.
Figure 4B:
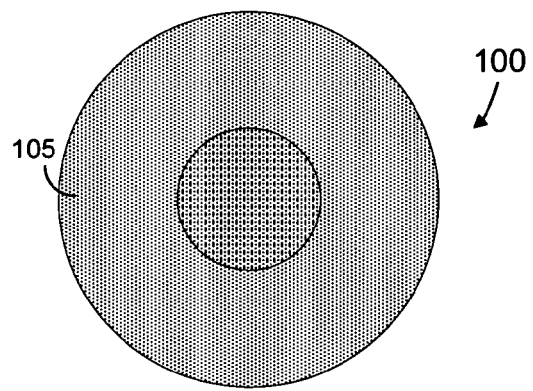

At step 91, a plurality of elements is placed between a megavoltage radiation source and an imaging device. The elements may comprise an array of beam-attenuating elements and may be mounted in accessory tray 80 of treatment head 101. FIGS. 4A and 4B illustrate an element of such an array according to some embodiments.

Element 100 may comprise tungsten and/or any other material suitable for the implementations described herein. FIG. 4A illustrates a physical relationship between element 100 and radiation source 200 according to some embodiments. As shown, radiation emitted from radiation source 200 follows a divergent path delineated by dotted lines 115 and 120. Outer surface 105 of element 100 is substantially aligned with the divergent path according to some embodiments. Axis 110 of element 100 is also substantially aligned with the divergent path (i.e., with an axis of the divergent path). Axis 110 may or may not necessarily be aligned with axis 102 of FIG. 1.

According to some embodiments, element 100 comprises a truncated cone. Element 100 may be substantially pointed toward a focal spot of the megavoltage radiation source according to some embodiments. Elements pointed toward a focal spot may be less disruptive of true scatter distribution than unfocused elements having a same physical cross-section. Generally, the composition and dimensions of element 100 are intended to produce a substantially circular area on imaging device 40 that includes a substantially determinable and spatially uniform amount of primary photons. Any other photons located in the area may therefore be assumed to comprise scatter radiation.

Figure 5:
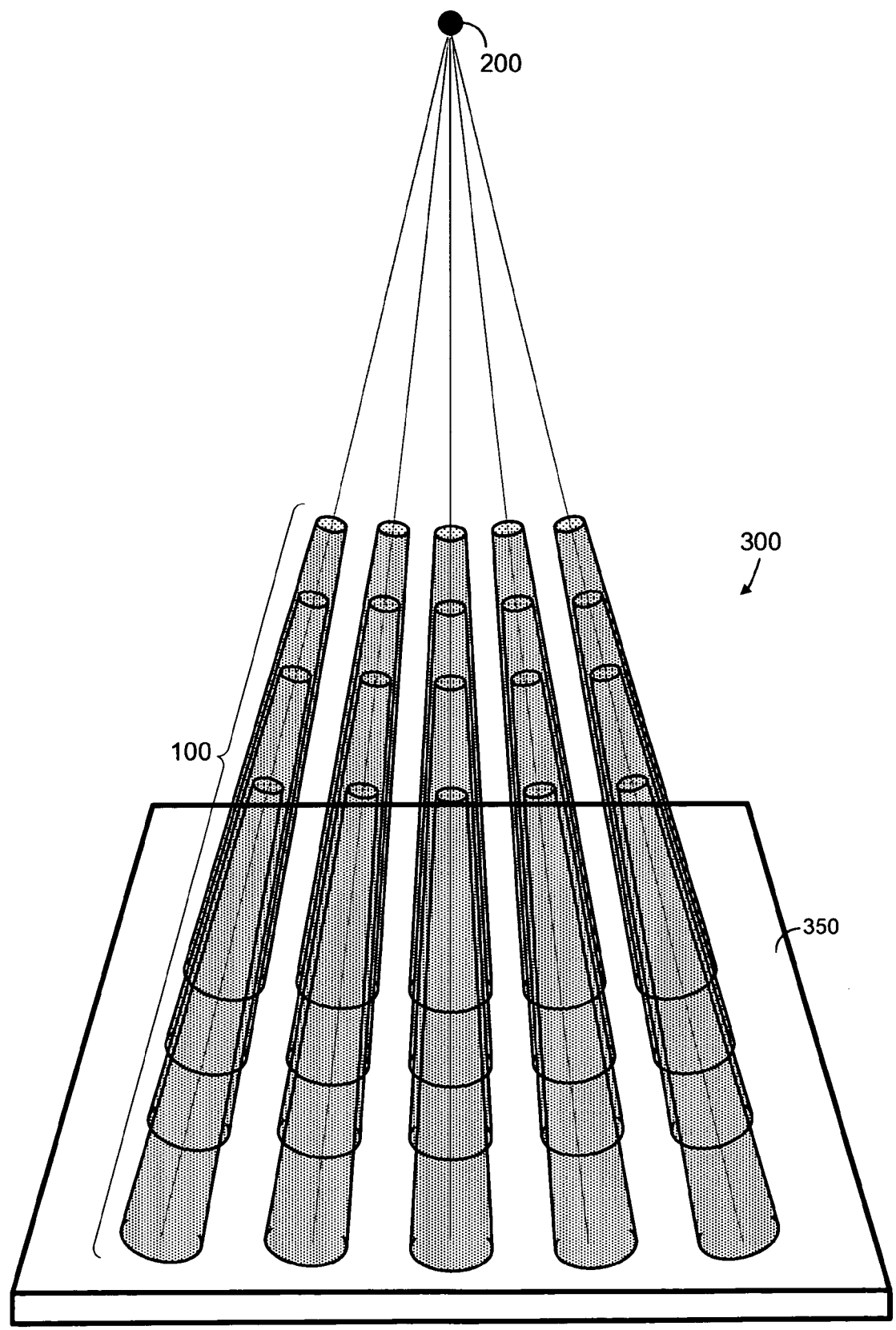
FIG. 5 is a perspective view of an array of beam-attenuating elements according to some embodiments.

FIG. 5 is a perspective view of array 300 of elements 100 that may be used in some embodiments of step 91. Array 300 includes support 350 that may comprise a Lucite™ block. Each element 100 in array 300 is pointed toward a focal spot of megavoltage radiation source 200. As shown, each element 100 is substantially aligned with one of the myriad of divergent paths traveled by photons emitted from source 200. Surfaces of elements 100 that are closest to source 200 may approximate a spherical surface to contribute to the uniformity in size and circular shape of the area produced thereby on imaging device 40. These areas will not be perfectly circular according to some embodiments because imaging device 40 is only an approximation of a spherical surface.

Figure 6:
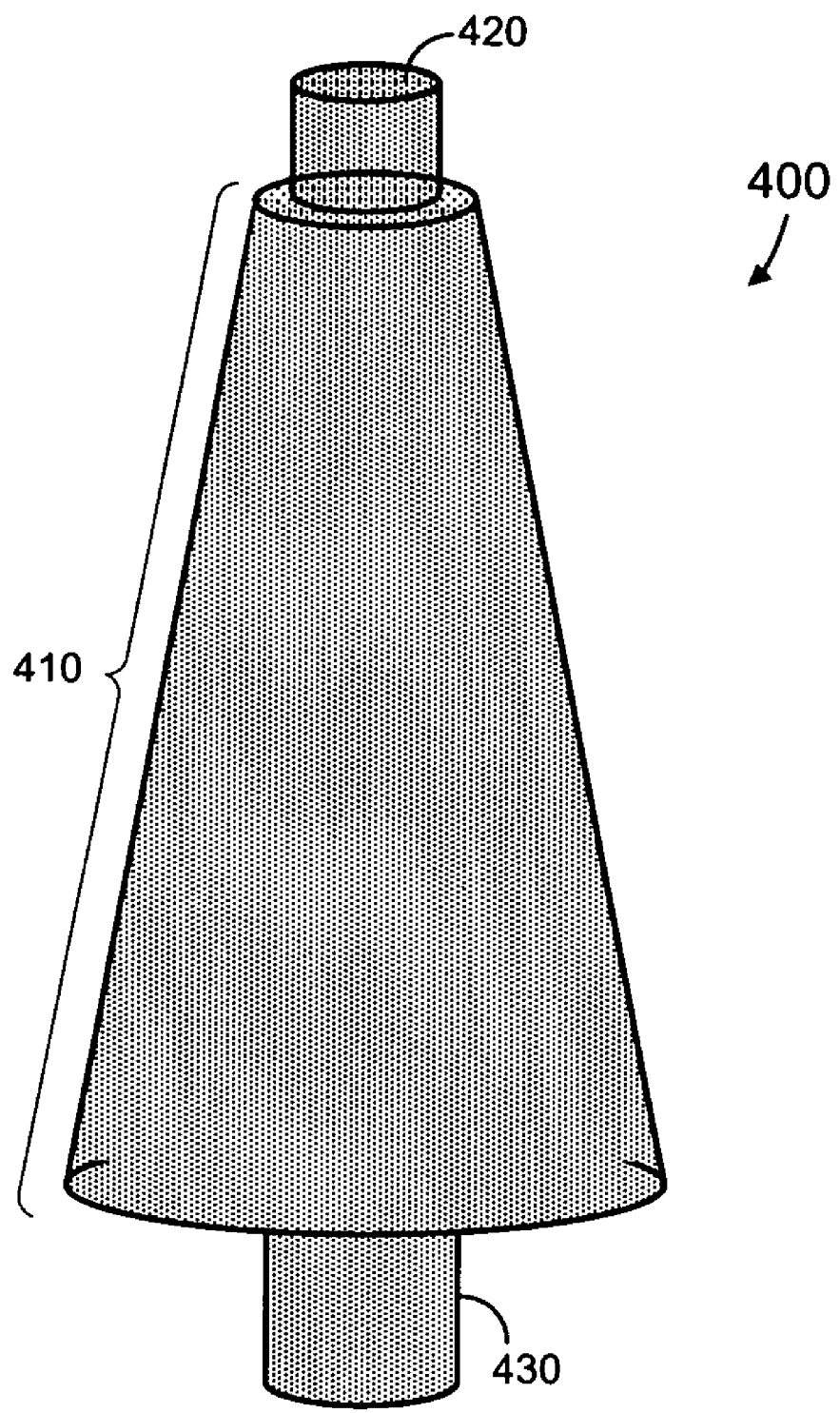
FIG. 6 is a perspective view of a beam-attenuating element according to some embodiments.

FIG. 6 is a perspective view of element 400 that may be used according to some embodiments of step 91. Portion 410 of element 400 comprises a truncated cone having an outer surface and an axis that may be substantially aligned with a divergent radiation path. Element 400 may also comprise tungsten and/or any other suitable composition.

Figure 7A:
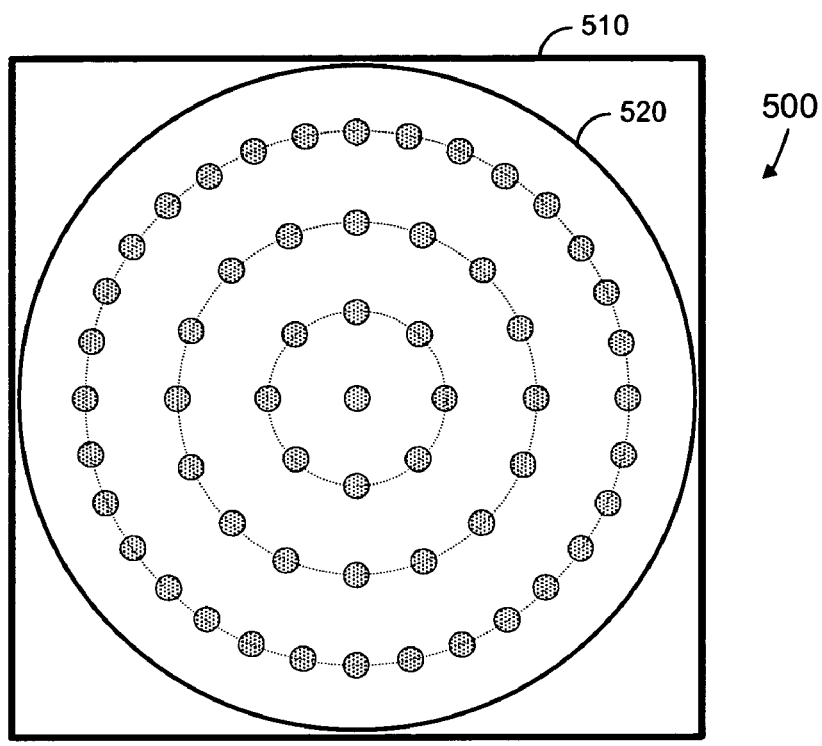
FIGS. 7A and 7B comprise a front perspective view and a cross-sectional side view of an array of beam-attenuating elements according to some embodiments.
Figure 7B:
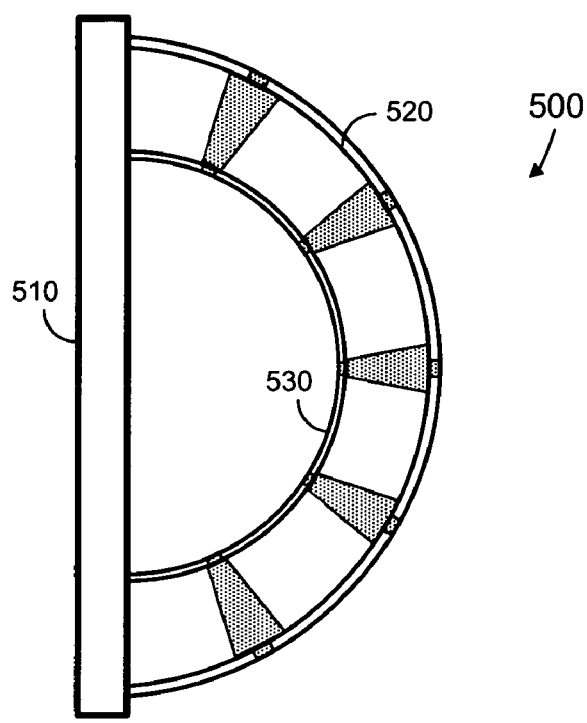

Element 400 further comprises cylindrical projections 420 and 430 to facilitate mounting in an array of elements according to some embodiments. FIGS. 7A and 7B comprise a top view and a cross-sectional side view, respectively, of array 500 of elements 400 according to some embodiments. Array 500 includes support 510, outer shell 520, and inner shell 530.

Figure 8:
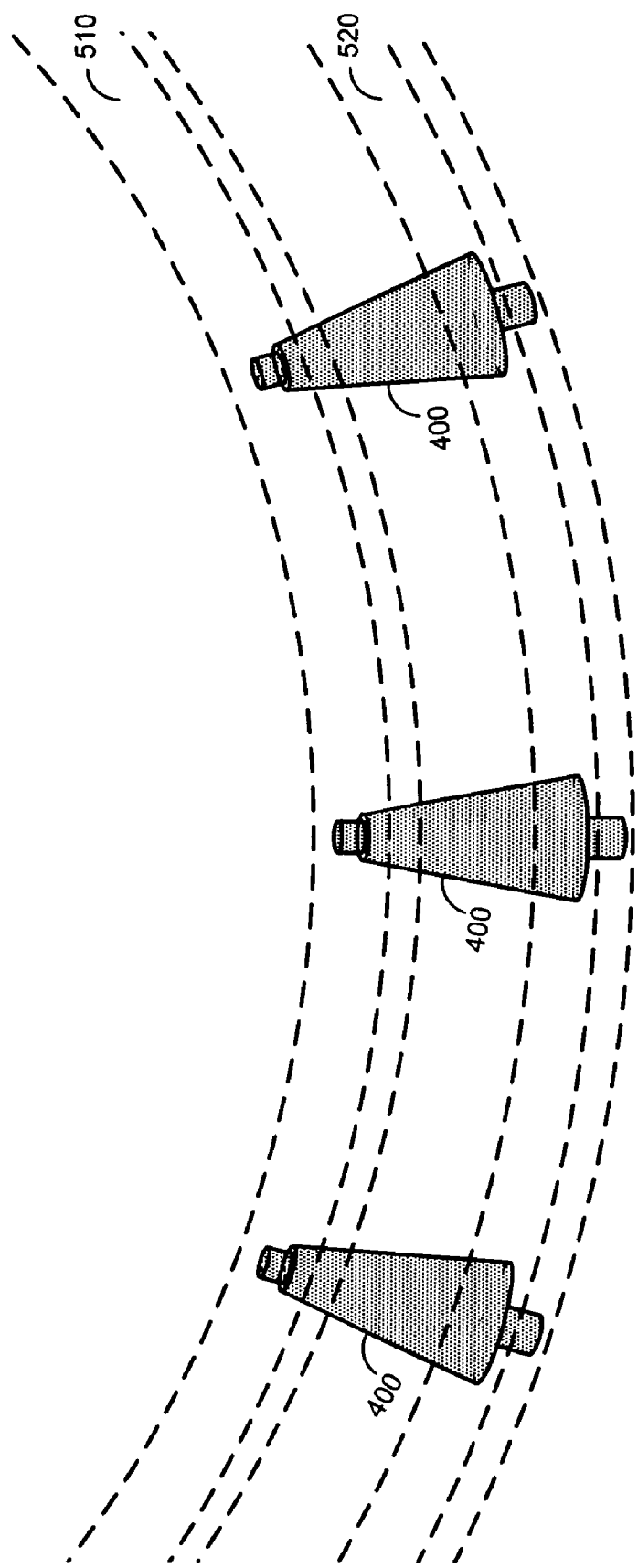
FIG. 8 comprises a transparent view of beam-attenuating elements within an array of beam-attenuating elements according to some embodiments.

Elements 400 are arranged in a circular pattern and shells 520 and 530 are both substantially spherical. Support 510, outer shell 520 and inner shell 530 may also comprise Lucite™. FIG. 8 provides additional detail of outer shell 510, inner shell 520, and elements 400 in a transparent sectional view. Array 500 may provide secure positioning of elements 400 and may produce substantially uniform and circular areas on imaging device 40.

Returning to process steps 90, first megavoltage radiation is emitted from the megavoltage radiation source at step 92. The first megavoltage radiation may intercept the plurality of elements and be attenuated thereby. The attenuated radiation and other radiation (e.g., scatter radiation) then proceed to the imaging device.

Accordingly, a first image is acquired at step 93 while the first megavoltage radiation is emitted from the megavoltage radiation source and while the plurality of elements is between the megavoltage radiation source and the imaging device. The first image includes areas corresponding to the plurality of elements, with each of these areas representing radiation attenuated by a respective element and scatter radiation. The first image and the corresponding areas will be described in more detail below.

Next, at step 94, an amount of scatter radiation is determined based at least on areas of the acquired image corresponding to the plurality of elements. Processes for determining the amount of radiation at step 94 will be described in detail below. Generally, step 94 may comprise determining a corresponding area of the acquired image for each element and determining an amount of non-scatter radiation for each of the areas, where the amount of non-scatter radiation for an area includes radiation that has passed through an element corresponding to the area.

Figure 9A:
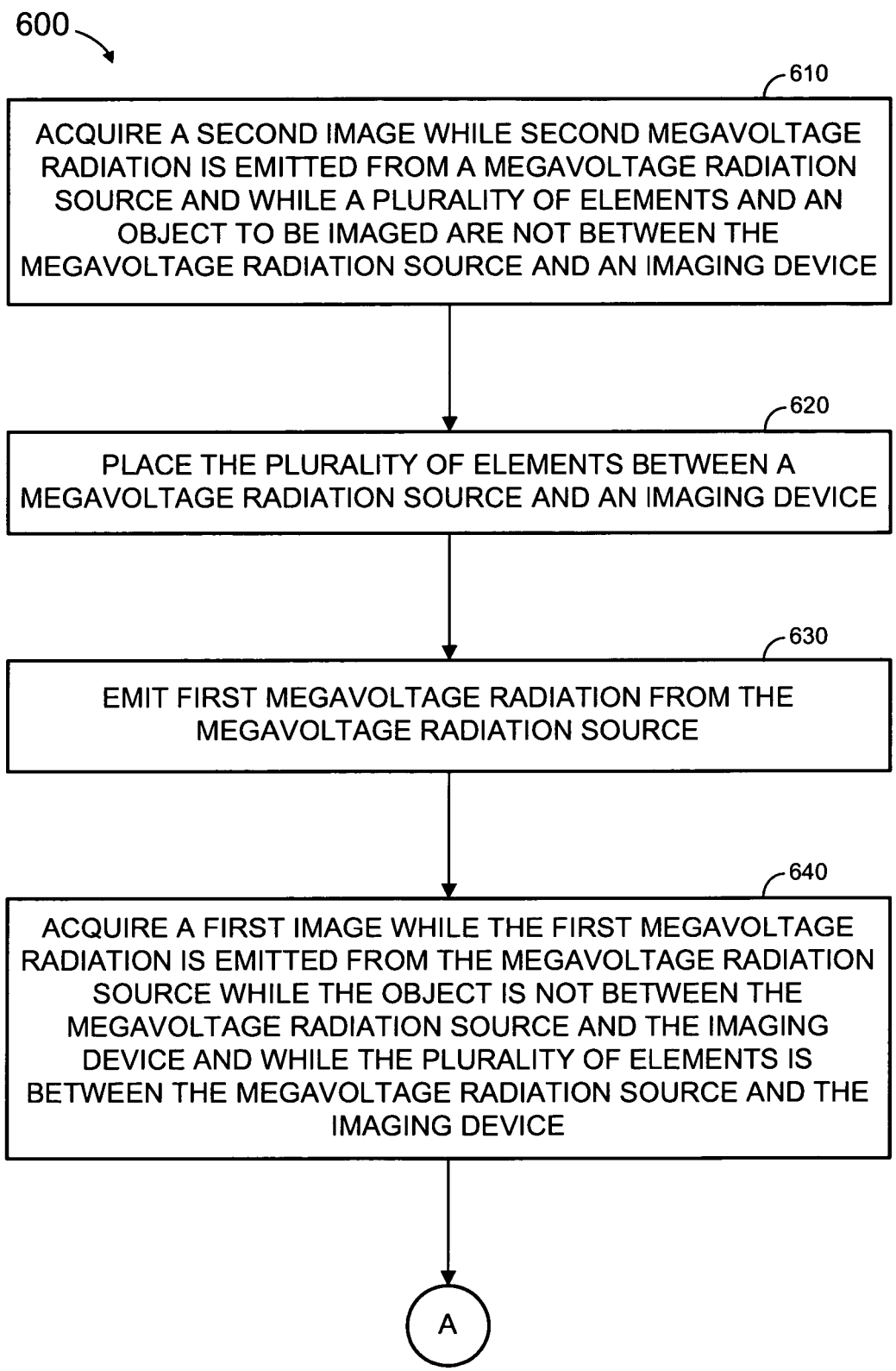
FIGS. 9A and 9B comprise a flow diagram of process steps pursuant to some embodiments.
Figure 9B:
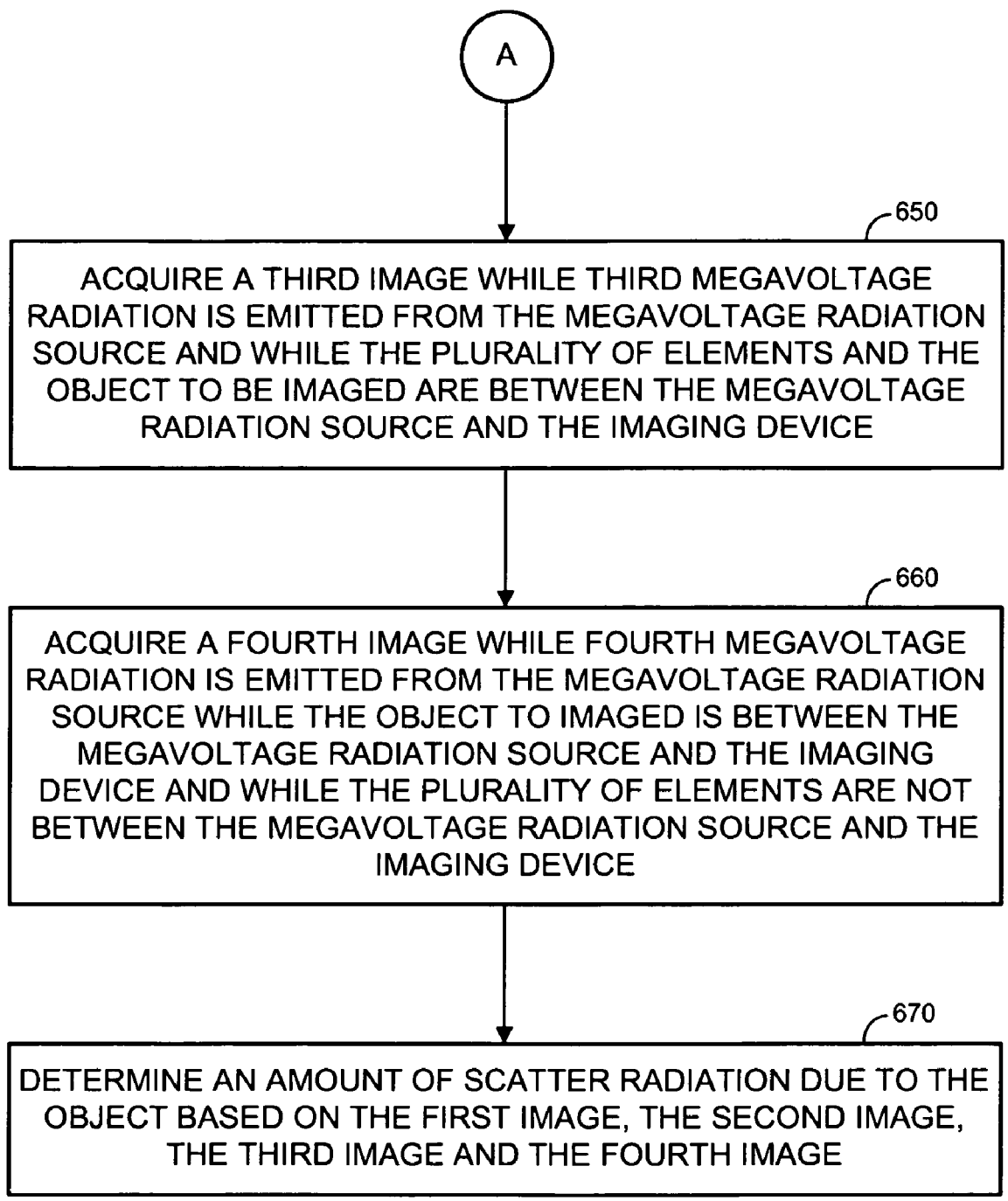

FIGS. 9A and 9B illustrate process steps 600 to determine an amount of scatter radiation according to some embodiments. Initially, at step 610, a second image is acquired while second megavoltage radiation is emitted from a megavoltage radiation source and while a plurality of elements and an object to be imaged are not between the megavoltage radiation source and an imaging device. Step 610 refers to a "second" image and "second" radiation to achieve consistency with the use of the terms "first" image and "first" radiation with respect to process steps 90. The terms "first", "second", "third" and "fourth" are not, in fact, intended to indicate a specific order in which images are acquired according to process steps 600.

According to the foregoing example, the object to be imaged comprises a pelvic phantom. Accordingly, the second image is acquired by imaging device 40 while neither the pelvic phantom nor a plurality of elements is between imaging device 40 and megavoltage radiation source (i.e., treatment head) 101.

Figure 10:
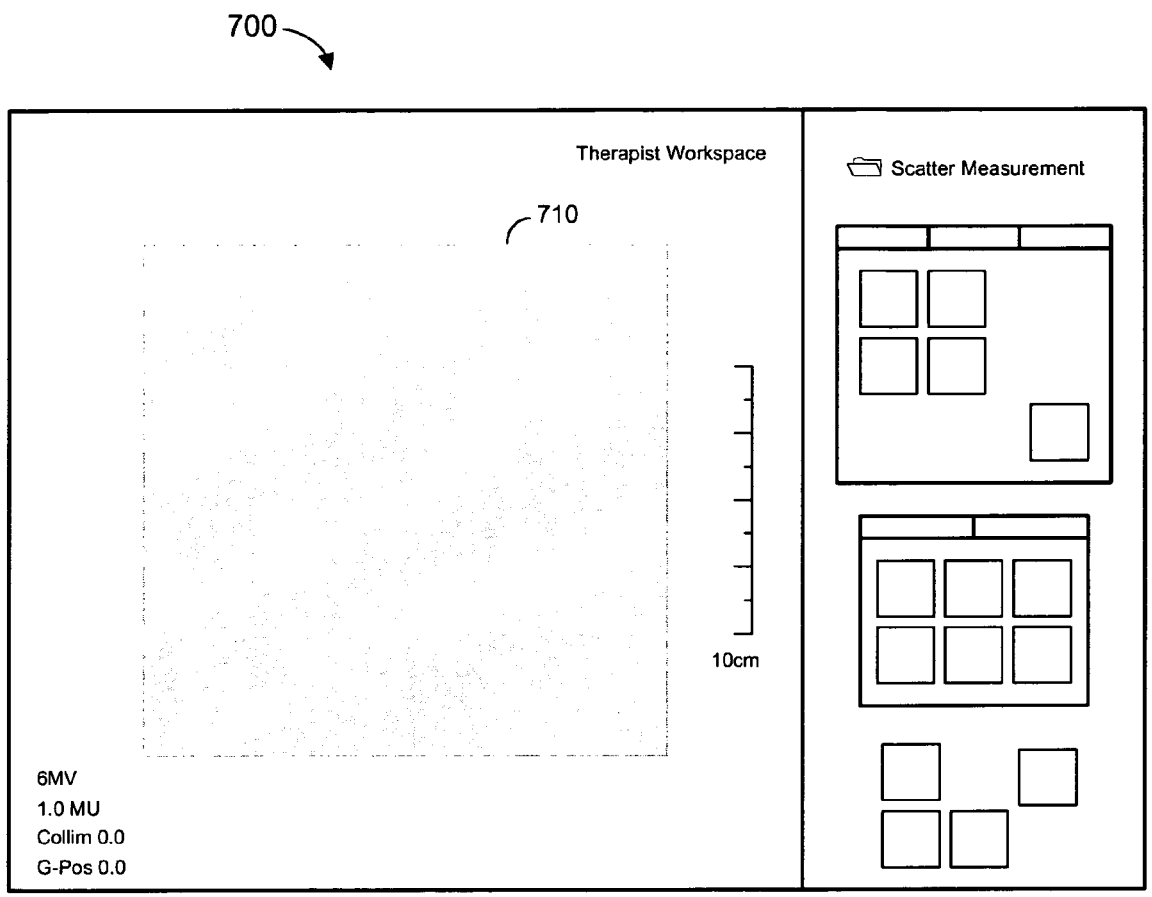
FIG. 10 is a view of a graphical interface of a linear accelerator system presenting an image acquired according to some embodiments.

FIG. 10 is an outward view of interface 700 displayed by output device 202 and including acquired image 710 acquired at step 610 according to some embodiments. Interface 700 may be provided by executing program code of a system control application such as, but not limited to, the COHERENCE™ workspace or the KONRAD™ treatment planning system sold by Siemens Medical Solutions.

Image 710 represents a field of the second megavoltage radiation that intercepts imaging elements within a detecting plane of imaging device 40. Image 710 is substantially uniform due to a lack of any radiation-attenuating structure between radiation source 110 and imaging device 40. The photon fluence at imaging device 40 that is represented by image 710 will be referred to herein as $\phi_0(x,y)$, where x and y are Cartesian coordinates of the detecting plane.

At step 620, a plurality of elements is placed between a megavoltage radiation source and an imaging device. The elements may comprise an array of beam-attenuating elements and may be mounted in accessory tray 80 of treatment head 101 as described above with respect to step 91 of process steps 90. The elements may be similar to or different from element 100 and element 400 described above, and the array may share qualities of array 300 and/or array 500. Any suitable elements or array may be used in conjunction with some embodiments.

First megavoltage radiation is emitted from the megavoltage radiation source at step 630. Step 630 may proceed as described above with respect to step 92. A first image is then acquired at step 640 while the first megavoltage radiation is emitted from the megavoltage radiation source and while the plurality of elements is between the megavoltage radiation source and the imaging device. As mentioned above, the first image includes areas corresponding to the plurality of elements, with each of these areas representing radiation attenuated by a respective element and scatter radiation.

Figure 11:
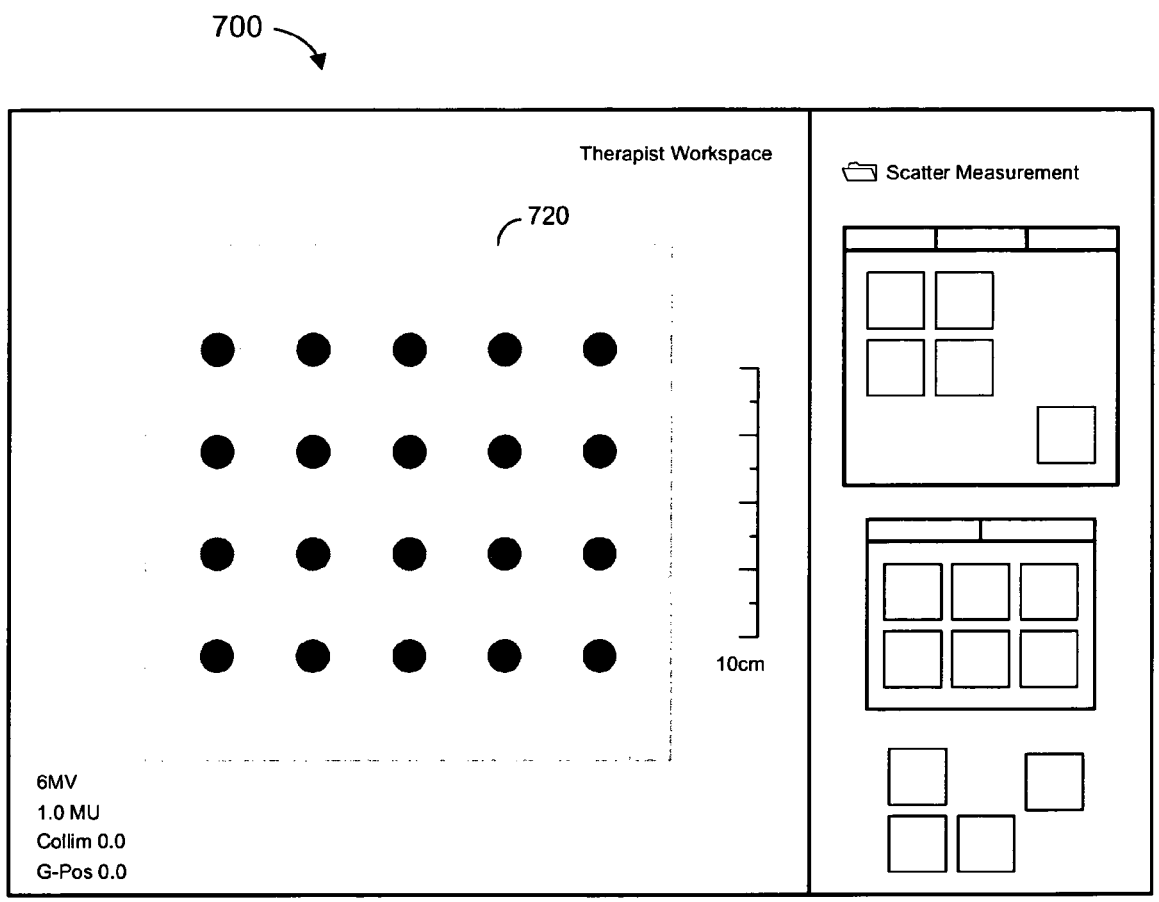
FIG. 11 is a view of a graphical interface of a linear accelerator system presenting an image acquired according to some embodiments.

FIG. 11 illustrates first image 720 acquired according to some embodiments. Image 720 includes twenty substantially-circular areas, with each area corresponding to one of the plurality of elements placed between megavoltage radiation source 101 and imaging device 40. According to some embodiments, each of the areas includes a substantially determinable and spatially uniform amount of primary photons, as well as an amount of scatter radiation. The photon fluence at the detecting plane of imaging device 40 that is represented by image 720 will be referred to herein as $\phi_1(x,y)$.

Next, at step 650, a third image is acquired while third megavoltage radiation is emitted from the megavoltage radiation source and while the plurality of elements and the object to be imaged are between the megavoltage radiation source and the imaging device. The third image therefore represents radiation attenuated by the plurality of elements and radiation attenuated (and scattered) by the object to be imaged. The photon fluence at the detecting plane that is represented by the third image will be referred to herein as $\phi_2(x,y)$.

According to the present example, the pelvic phantom is placed on table 50 prior to step 650 and while an array of elements is disposed in accessory tray 80. Linear accelerator 10 is operated to emit the third megavoltage radiation and imaging device 40 acquires an image based thereon.

Figure 12:
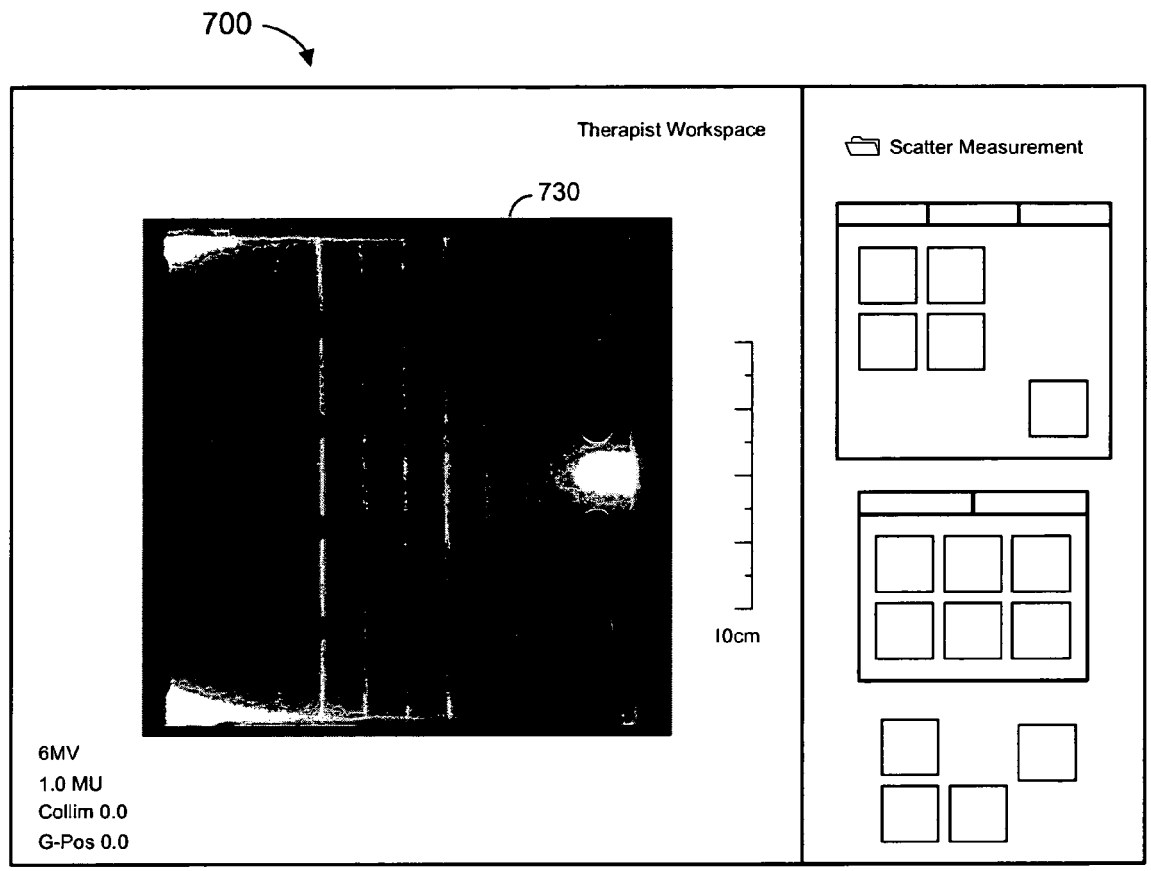
FIG. 12 is a view of a graphical interface of a linear accelerator system presenting an image acquired according to some embodiments.

FIG. 12 illustrates interface 700 including third image 730 acquired according to some embodiments of step 650. Image 730 represents radiation attenuated by the plurality of elements, radiation attenuated by the object to be imaged, and radiation scattered by the object. Image 730 may also represent radiation scattered by the plurality of elements, but such scatter radiation may be negligible in comparison to the radiation scattered by the object.

A fourth image is acquired at step 660. The fourth image is acquired while fourth megavoltage radiation is emitted from the megavoltage radiation source, while the object to be imaged is between the megavoltage radiation source and the imaging device, and while the plurality of elements is not between the megavoltage radiation source and the imaging device. The fourth image therefore represents radiation attenuated and scattered by the object to be imaged. $\phi_3(x,y)$ will refer to the photon fluence at the detecting plane of imaging device 40 that is represented by the fourth image.

The plurality of elements may simply be removed from between radiation source 101 and imaging device 40 after step 650 and before step 660. According to some embodiments, the pelvic phantom remains on table 50 and linear accelerator 10 is operated to emit the fourth megavoltage radiation. Imaging device 40 may therefore acquire the fourth image at step 660 based on the emitted fourth megavoltage radiation.

Figure 13:
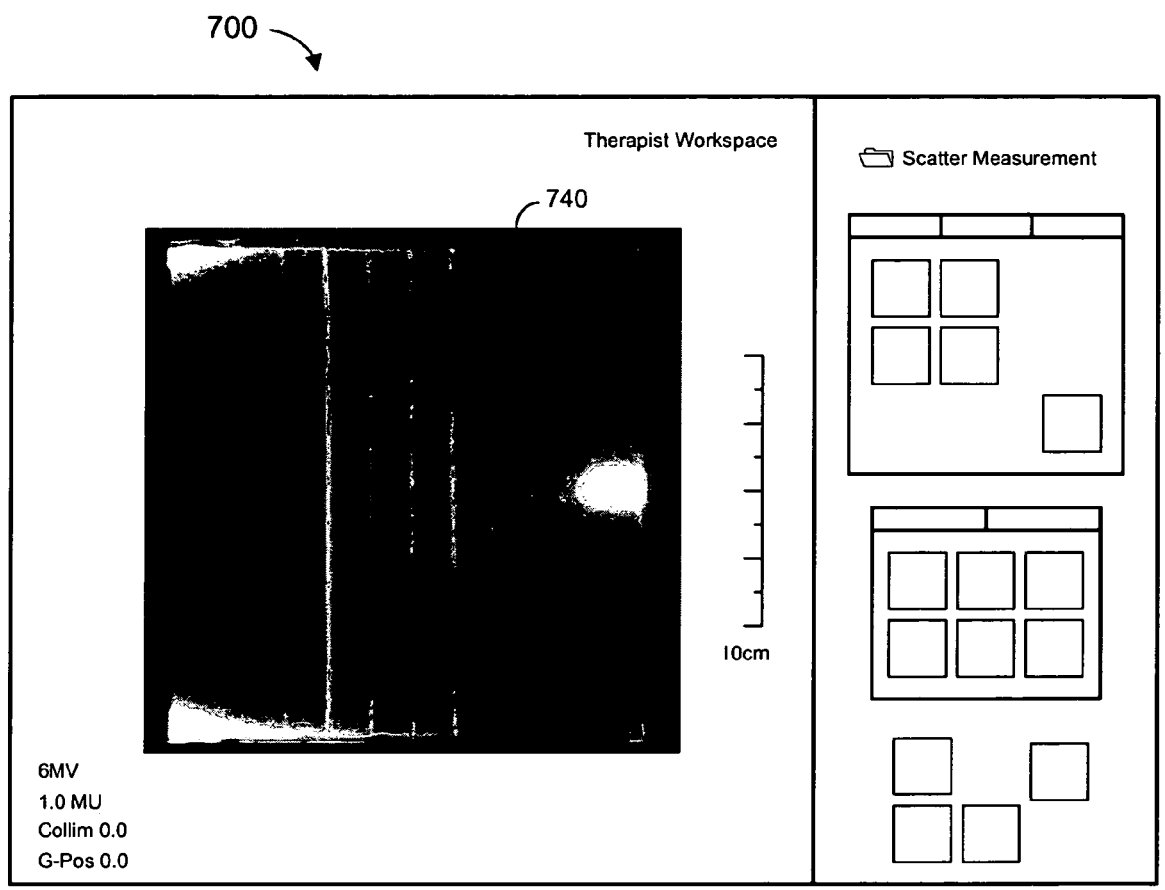
FIG. 13 is a view of a graphical interface of a linear accelerator system presenting an image acquired according to some embodiments.

FIG. 13 illustrates fourth image 740 acquired according to some embodiments of step 660. Image 740 represents radiation that is attenuated and radiation that is scattered by the pelvic phantom of the present example. The light vertical lines of image 740 represent strongly-attenuative materials of the pelvic phantom that are intended to provide landmarks and/or a known scale to images of the pelvic phantom.

An amount of radiation scatter due to the object is determined at step 670. The determination is based on the first image ($\phi_1(x,y)$), the second image ($\phi_0(x,y)$), the third image ($\phi_2(x,y)$), and the fourth image ($\phi_3(x,y)$).

According to some embodiments of step 670, the substantially-circular areas are identified, and an amount of non-scatter radiation is determined for each of the areas. The amount of non-scatter radiation for an area includes megavoltage radiation that has passed through an element corresponding to the area. The amount of non-scatter radiation determined for an area may be subtracted from the area, and the radiation remaining in the area is assumed to consist of scatter radiation. Next, the scatter radiation is spatially extrapolated over the entire radiation field to generate a scatter radiation image. The scatter radiation image may be subtracted from the image of the object (e.g., the fourth image) to obtain a scatter-corrected image.

In some specific embodiments of step 670, the first image representing fluence $\phi_1(x,y)$ is processed to extract values of the first image in the substantially-circular areas. For example, areas of the first image centered close to the center of each area are extracted. The ith element of the array produces a corresponding area contained in subimage $g_i$ (each subimage contains the substantially-circular area corresponding to a single element only).

For each subimage $g_i$, a set $\Omega_i$ is found that contains the values of all pixels that fall below a specified percentile rank (e.g., the 5th percentile). The mean or median value of all pixels in $\Omega_i$ is taken as the estimate $s_i$ of the scatter radiation in the substantially-circular area of the subimage. The value $s_i$ is associated with the coordinate pair $(x^i_s, y^i_s)$ that represents an estimated location of the area's center. This center position can be estimated by determining an inverse intensity-weighted center of mass of the pixels in $\Omega_i$. The foregoing is repeated for each subimage $g_i$ to produce i scatter measurements $s_i$ $(x^i_s, y^i_s)$.

The attenuation of megavoltage radiation through the points $(x^i_s, y^i_s)$ may be modeled by the foregoing three equations in view of the fluences represented by the first through fourth images.

(1) $\phi_1(x^i_s, y^i_s) = \phi_0(x^i_s, y^i_s) e^{-\mu_b l_b}$, where $\mu_b$ is the effective linear attenuation coefficient of a corresponding element and $l_b$ is the length of the element.

(2) $\phi_2(x^i_s, y^i_s) = \phi_0(x^i_s, y^i_s) e^{-\mu l}(e^{-\int_{P_o} \mu_o(x) dx}) + S(x^i_s, y^i_s)$, where $\mu_o(P)$ is the linear attenuation coefficient of the imaged object at point $x \in R^3$ along the ray path $P_o$, and $S(x^i_s, y^i_s)$ represents scatter radiation due to the imaged object.

(3) $\phi_3(x^i_s, y^i_s) = \phi_0(x^i_s, y^i_s) e^{-\int_{P_o} \mu_o(x) dx} + S(x^i_s, y^i_s)$, where $\mu_o(P)$ is the linear attenuation coefficient of the imaged object at point $x \in R^3$ along the ray path $P_o$.

An image $S_f$ representing scatter radiation may be determined by substituting (1) and (3) into (2) to yield:

$$S_f(x^i_s, y^i_s) = (f_0 f_2 - f_1 f_3)/(f_0 - f_1),$$

where $f_0$ through $f_3$ denote the first image through the fourth image, respectively, and where the coordinate notations on the right-hand-side expression have been suppressed for clarity.

Figure 14:
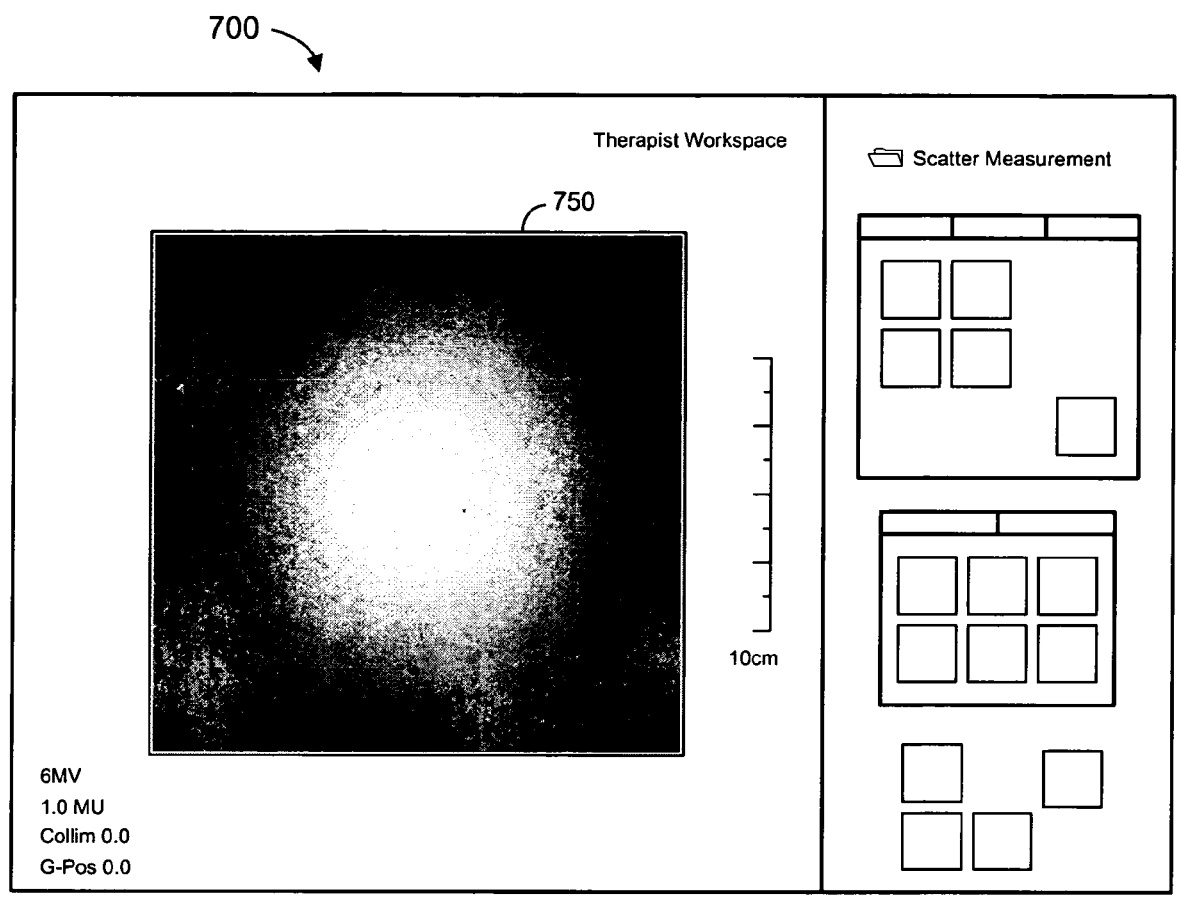
FIG. 14 is a view of a graphical interface of a linear accelerator system presenting an image acquired according to some embodiments.

The scatter radiation values $S_f(x^i_s, y^i_s)$ are valid only within the substantially-circular areas. The values may therefore be interpolated to the full resolution of imaging device 40 using an interpolation method such as bicubic spline interpolation. The interpolated scatter radiation distribution $S_d(x^i_s, y^i_s)$ may comprise the amount of scatter radiation determined at 670. FIG. 14 illustrates interface 700 displaying scatter radiation image 750 representing scatter radiation distribution $S_d(x^i_s, y^i_s)$ according to the present example.

Figure 15:
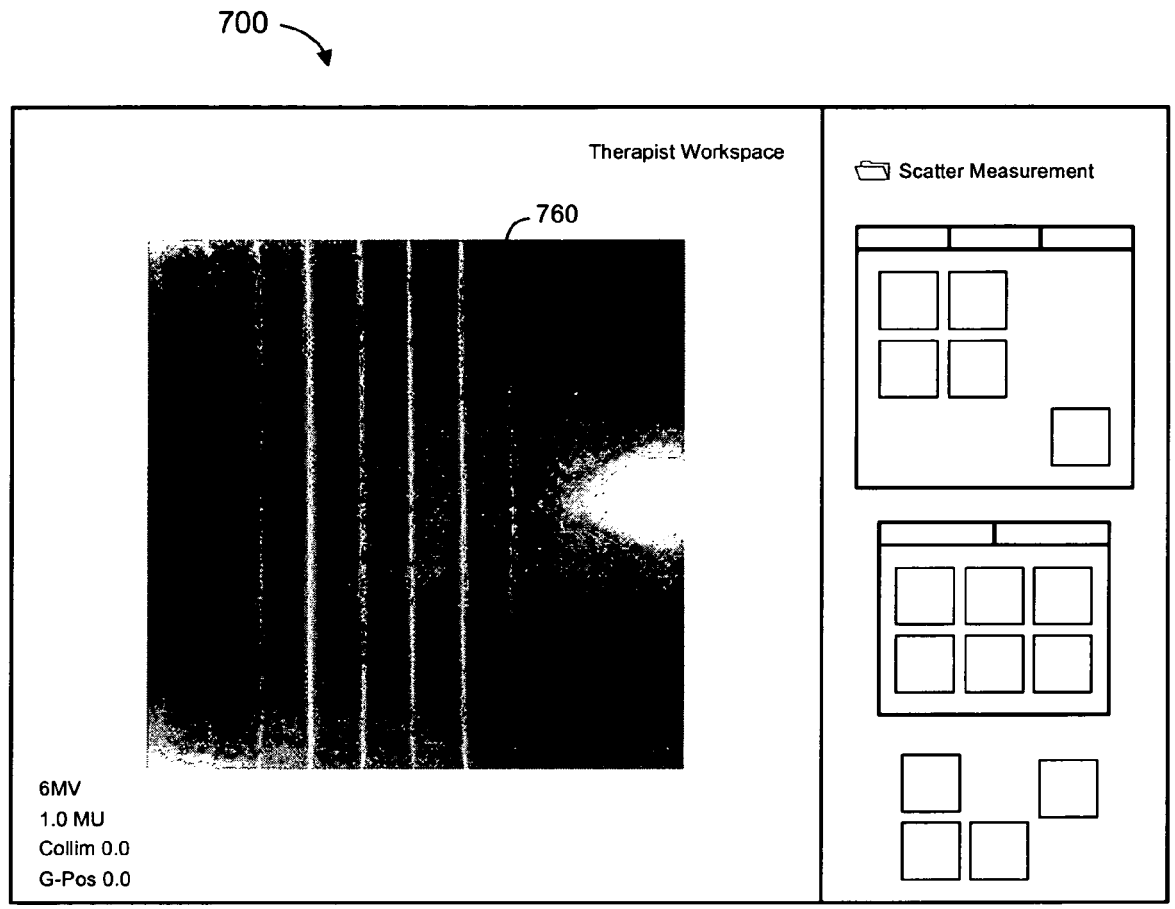
FIG. 15 is a view of a graphical interface of a linear accelerator system presenting an image acquired according to some embodiments.

In some embodiments, the scatter radiation distribution $S_d(x^i_s, y^i_s)$ may be subtracted from the fourth image $f_3(x^i, y^i)$ to obtain a scatter-corrected image $f(x^i, y^i)$ of the imaged object. Interface 700 of FIG. 15 displays such a scatter-corrected image according to some embodiments.

Figure 16:
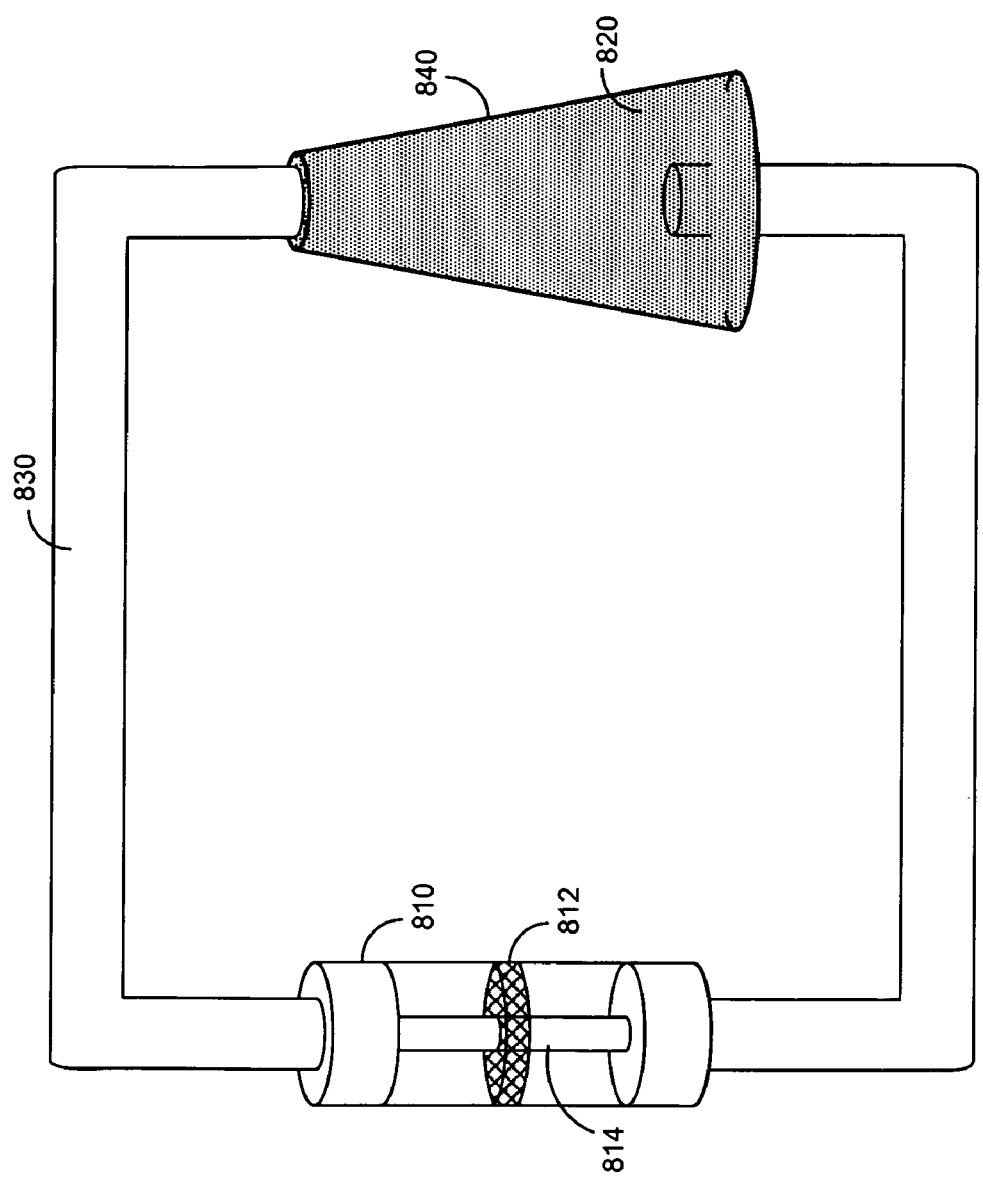
FIG. 16 is a view of a system to provide a beam-attenuating element according to some embodiments.

FIG. 16 is an outward view of system 800 according to some embodiments. System 800 comprises a sealed hydraulic circuit including pump 810 comprising magnetic material 812 for actuating dual-headed plunger 814, dense fluid 820 (e.g., metallic mercury), non-metallic fluid 830 and chamber 840, which may comprise a truncated cone. In operation, pump 810 pumps dense fluid 820 into and out of chamber 840 depending on whether beam attenuation is desired. System 800 may be used to efficiently insert and remove a beam-attenuating element from between a megavoltage radiation source and an imaging device. System 800 also allows efficient adjustment of a level of beam attenuation based on an amount of fluid 820 pumped into chamber 840.

Figure 17:
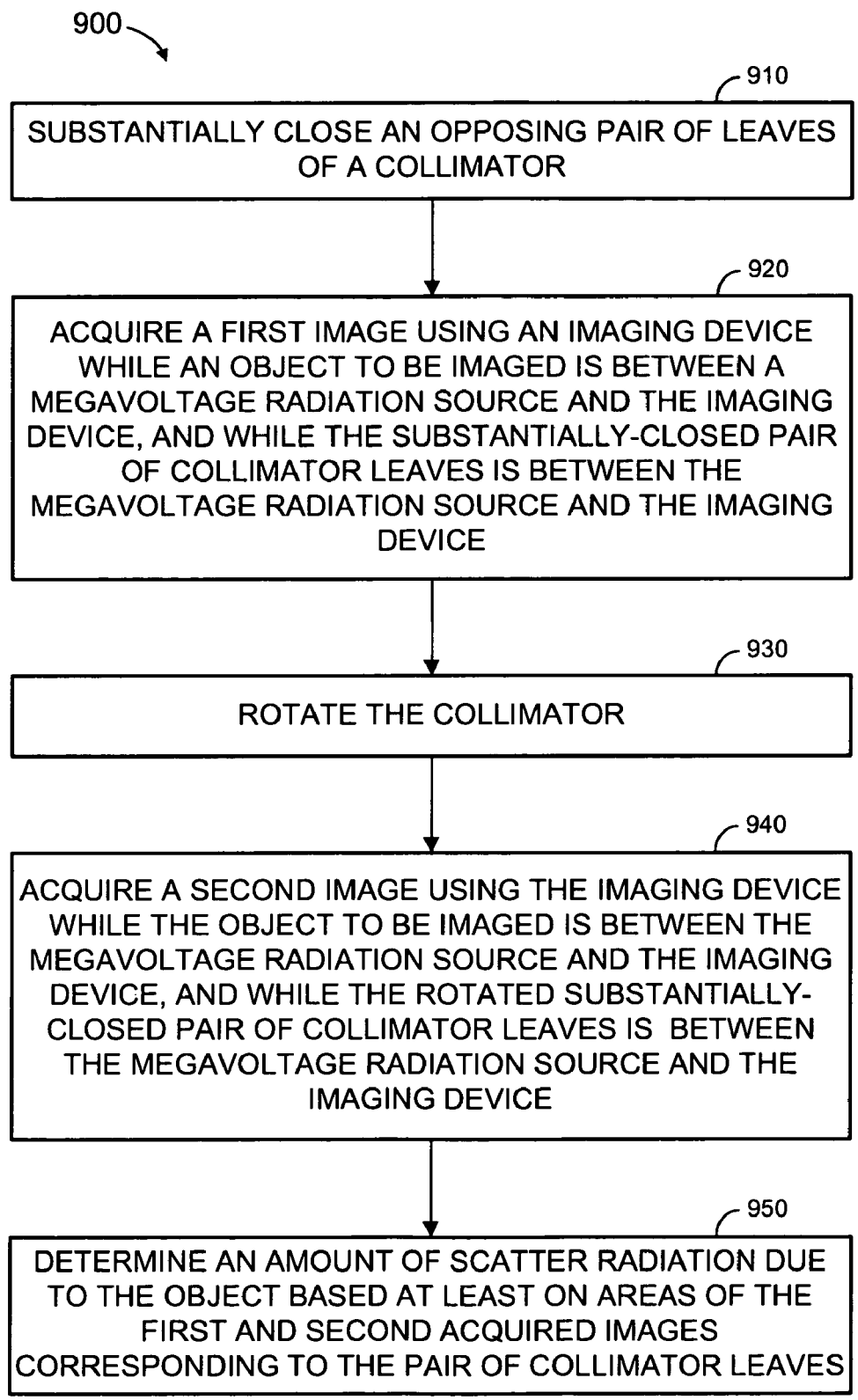
FIG. 17 is a flow diagram of process steps according to some embodiments.

FIG. 17 is a diagram of process steps 900 to determine an amount of scatter radiation according to some embodiments. Some embodiments of process steps 900 do not require an array of beam-attenuating elements as described above. Rather, leaves of a multileaf collimator are used to produce areas within an acquired image from which scatter radiation may be determined.

An opposing pair of leaves of a collimator is substantially closed at step 910. The pair of leaves is substantially closed in order to block a portion of radiation emitted from a megavoltage radiation source. The blocked portion therefore does not reach a downstream imaging device.

According to some embodiments of step 910, operator console 20 controls an opposing pair of leaves of jaws 73 and 74 to close completely, which may or may not result in a small gap therebetween. Y-jaws 71 and 72 are opened to allow a suitable amount of radiation to be emitted from treatment head 101.

Figure 18A:
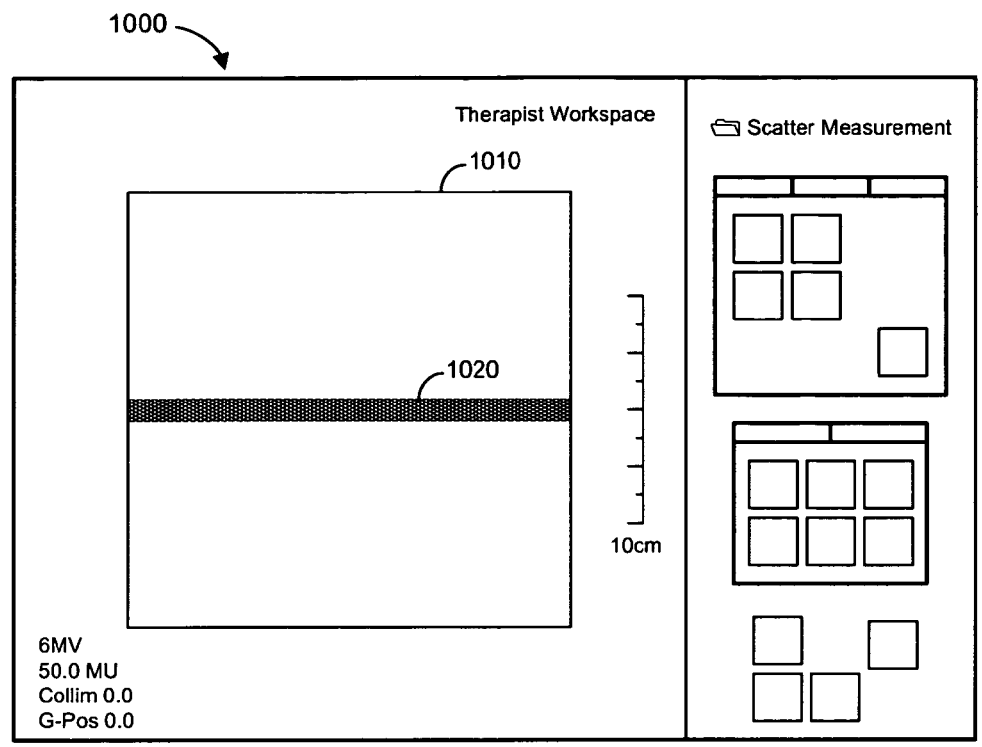
FIGS. 18A and 18B are views of graphical interfaces presenting images acquired according to some embodiments.

A first image is acquired at step 920 using an imaging device. The first image is acquired while the substantially-closed pair of leaves is between a megavoltage radiation source and an imaging device and while an object to be imaged is between the megavoltage radiation source and the imaging device. FIG. 18A illustrates interface 1000 presenting image 1010 acquired according to some embodiments of step 920. Image 1010 includes darkened area 1020 that is assumed to primarily represent scatter radiation.

Figure 18B:
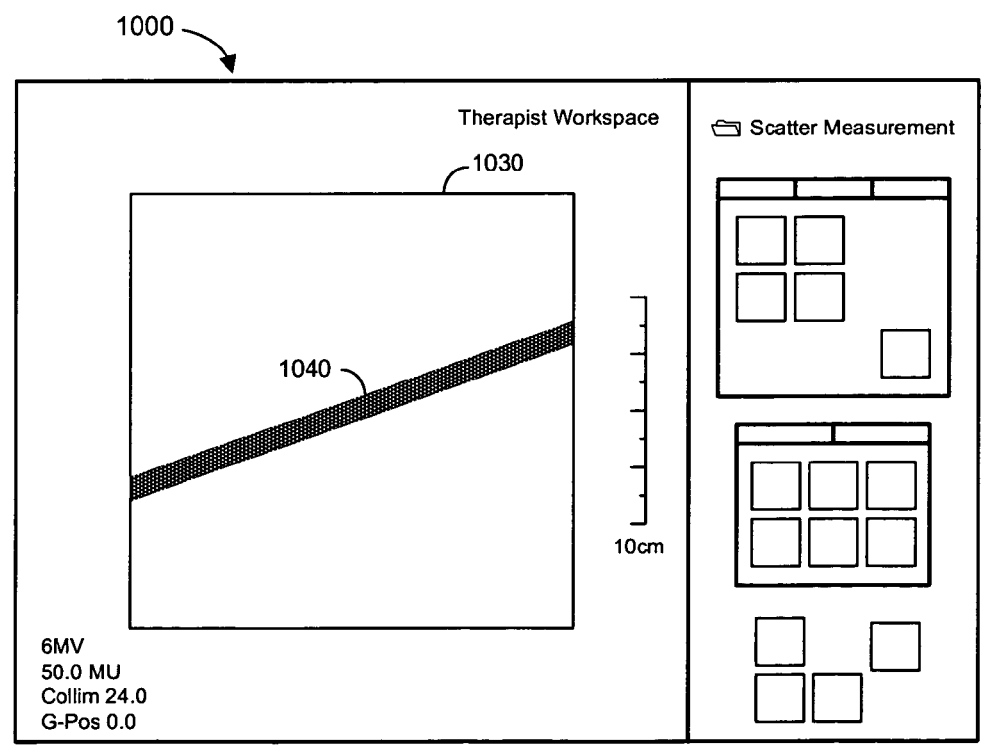

A collimator is rotated at step 930. The collimator may be rotated through any suitable arc according to some embodiments. For example, collimator 70 of treatment head 101 may be rotated twenty-four degrees at step 930. A second image is then acquired at step 940. The second image is acquired while the substantially-closed pair of leaves is between the megavoltage radiation source and the imaging device and while the object to be imaged is between the megavoltage radiation source and the imaging device. FIG. 18B illustrates interface 1000 presenting image 1030 acquired according to some embodiment, in which darkened area 1040 is assumed to primarily represent scatter radiation.

Next, at step 950, an amount of radiation scatter due to the object is determined. The determination is based at least on areas of the first and second images that correspond to the pair of collimator leaves. According to the present example, the determination is based on areas 1020 and 1040.

In some embodiments, scatter radiation values are determined based on pixel values within each of the areas. Scatter radiation values for the entire radiation field may then be interpolated as described above based on the determined scatter radiation values.

Figure 19A:
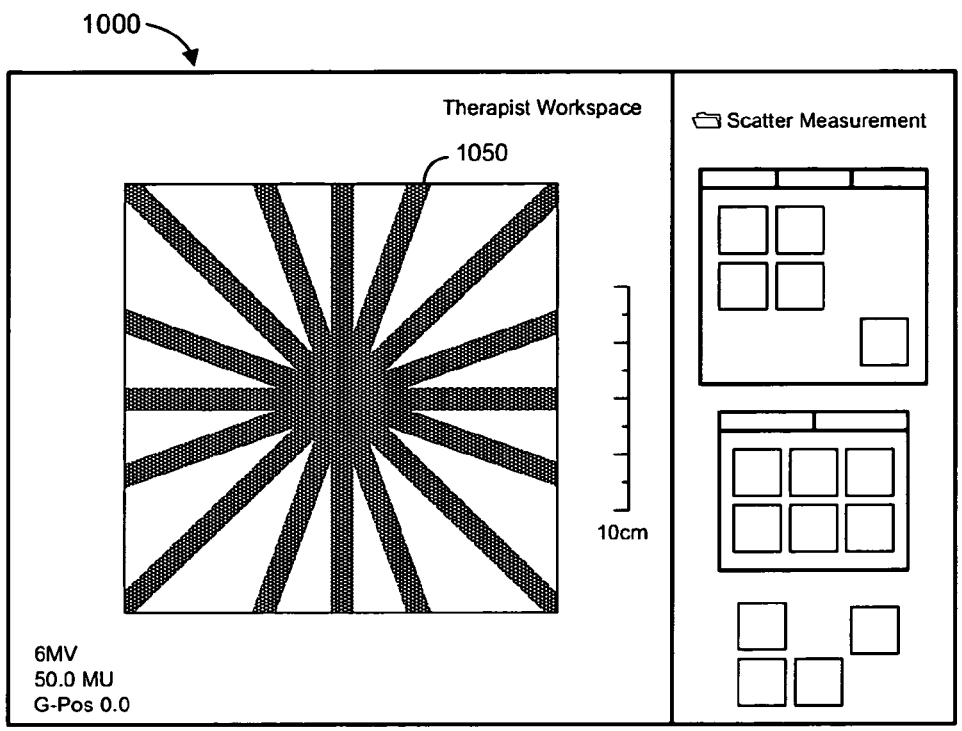
FIGS. 19A and 19B are views of graphical interfaces presenting images acquired according to some embodiments.

According to some embodiments of process steps 900, images are acquired for each of several collimator rotational positions. FIG. 19A illustrates image 1050 that is a combination of eight images acquired at eight different collimator positions. The determination at step 950 may be based on scatter radiation within each of the darkened areas of image 1050, thereby improving results of the above-mentioned interpolation.

Figure 19B:
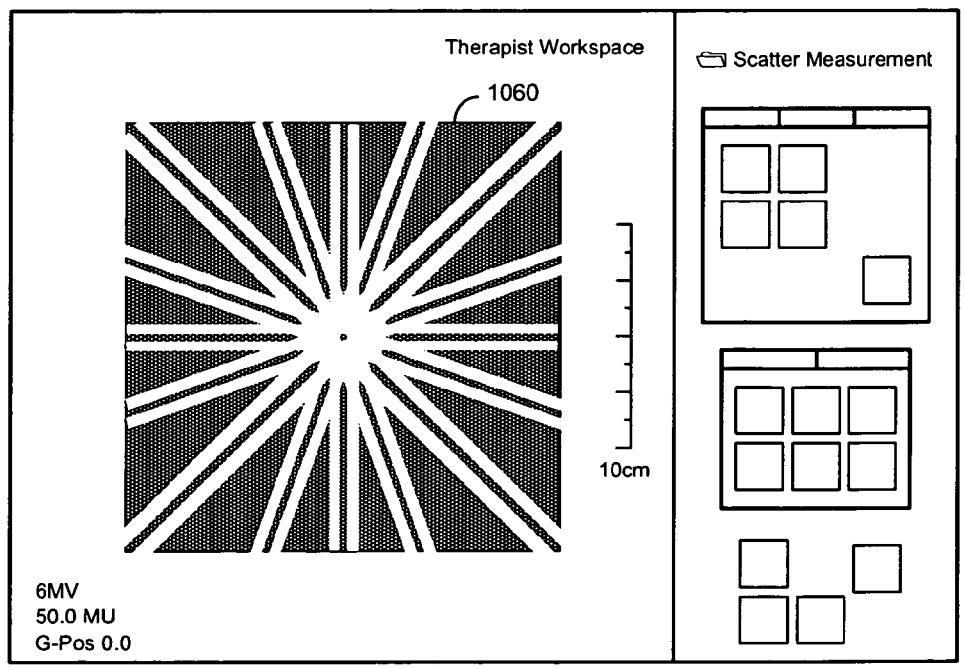

The outer edges of the pair of leaves may reduce scatter at the center of each darkened area, therefore each darkened area may underrepresent an amount of scatter radiation along its central long axis. Consequently, the amount of scatter radiation may be determined at step 950 based only on outer edges of each darkened area. FIG. 19B illustrates interface 1000 displaying image 1060. The white areas of image 1060 represent the outer edges of each darkened area of image 1050. Accordingly, scatter radiation values may be determined for the white areas and then interpolated over the entire imaging area to generate a scatter radiation image at step 950. The scatter radiation image may be used to correct subsequent images of the object.

The several embodiments described herein are solely for the purpose of illustration. Therefore, persons in the art will recognize from this description that other embodiments may be practiced with various modifications and alterations.

What is claimed is:

1. A method comprising:
    placing a plurality of elements between a megavoltage radiation source and an imaging device;
    emitting megavoltage radiation from the megavoltage radiation source;
    acquiring a first image while first megavoltage radiation is emitted from the megavoltage radiation source and while the plurality of elements is between the megavoltage radiation source and the imaging device; and
    determining an amount of scatter radiation based at least on areas of the acquired image corresponding to the plurality of elements, wherein an apex of each of the plurality of elements is pointed toward a focal spot of the megavoltage radiation source.

2. A method according to claim 1, wherein the emitted radiation follows a divergent path, and
    wherein an axis of at least one of the plurality of elements is substantially aligned with the divergent path.

3. A method according to claim 2, wherein an outer surface of at least one of the plurality of elements is substantially aligned with the divergent path.

4. A method according to claim 1, wherein determining the amount of scatter radiation comprises:
    for each element, determining a corresponding area of the acquired image; and
    determining an amount of scatter radiation for each of the corresponding areas.

5. A method according to claim 4, wherein determining the amount of scatter radiation for each of the areas comprises:
    determining an amount of non-scatter radiation for each of the areas, the amount of non-scatter radiation for an area comprising radiation that has passed through an element corresponding to the area.

6. A method according to claim 1, further comprising:
    acquiring a second image while second megavoltage radiation is emitted from the megavoltage radiation source and while the plurality of elements and an object to be imaged are not between the megavoltage radiation source and the imaging device;
    acquiring a third image while third megavoltage radiation is emitted from the megavoltage radiation source, and while the plurality of elements and the object to be imaged are between the megavoltage radiation source and the imaging device; and
    acquiring a fourth image while fourth megavoltage radiation is emitted from the megavoltage radiation source, while the object is between the megavoltage radiation source and the imaging device, and while the plurality of elements is not between the megavoltage radiation source and the imaging device,
    wherein determining the amount of scatter radiation comprises determining, for each of the corresponding areas, an amount of scatter radiation due to the object based on the first image, the second image, the third image, and the fourth image,
    wherein the object to be imaged is not between the megavoltage radiation source and the imaging device during acquisition of the first image.

7. A method according to claim 6, further comprising:
    modifying the fourth image based on the determined amount of scatter radiation.

8. A method according to claim 1, further comprising:
    acquiring a second image while second megavoltage radiation is emitted from the megavoltage radiation source, while an object is between the megavoltage radiation source and the imaging device, and while the plurality of elements is not between the megavoltage radiation source and the imaging device; and modifying the second image based on the determined amount of scatter radiation, wherein the object to be imaged is not between the megavoltage radiation source and the imaging device during acquisition of the first image.

9. An apparatus comprising:

a megavoltage radiation source to emit megavoltage radiation;

an imaging device to acquire an image based on megavoltage radiation; and a plurality of elements to attenuate megavoltage radiation emitted from the megavoltage radiation source before the attenuated megavoltage radiation reaches the imaging device, wherein an apex of each of the plurality of elements is pointed toward a focal spot of the megavoltage radiation source, wherein the emitted radiation follows a divergent path, and wherein an axis of at least one of the plurality of elements is substantially aligned with the divergent path.

10. An apparatus according to claim 9, wherein an outer surface of at least one of the plurality of elements is substantially aligned with the divergent path.

11. An apparatus according to claim 9, further comprising:

a processing device to:

acquire a first image while first megavoltage radiation is emitted from the megavoltage radiation source and while the plurality of elements is between the megavoltage radiation source and the imaging device; and determine an amount of scatter radiation based at least on areas of the acquired image corresponding to the plurality of elements.

12. An apparatus according to claim 9, wherein determination of the amount of scatter radiation comprises:

for each element, determination of a corresponding area of the acquired image; and determination of an amount of scatter radiation for each of the corresponding areas.

13. An apparatus according to claim 12, wherein determination of the amount of scatter radiation for each of the areas comprises:

determination of an amount of non-scatter radiation for each of the areas, the amount of non-scatter radiation for an area comprising radiation that has passed through an element corresponding to the area.

14. An apparatus according to claim 9, the processing device further to:

acquire a second image while second megavoltage radiation is emitted from the megavoltage radiation source and while the plurality of elements and an object to be imaged are not between the megavoltage radiation source and the imaging device;

acquire a third image while third megavoltage radiation is emitted from the megavoltage radiation source, and while the plurality of elements and the object to be imaged are between the megavoltage radiation source and the imaging device; and acquire a fourth image while fourth megavoltage radiation is emitted from the megavoltage radiation source, while the object is between the megavoltage radiation source and the imaging device, and while the plurality of elements is not between the megavoltage radiation source and the imaging device, wherein determination of the amount of scatter radiation comprises determination, for each of the corresponding areas, of an amount of scatter radiation due to the object based on the first image, the second image, the third image, and the fourth image, wherein the object to be imaged is not between the megavoltage radiation source and the imaging device during acquisition of the first image.

15. An apparatus according to claim 14, the processing device further to:

modify the fourth image based on the determined amount of scatter radiation.

16. An apparatus according to claim 9, the processing device further to:

acquire a second image while second megavoltage radiation is emitted from the megavoltage radiation source, while an object is between the megavoltage radiation source and the imaging device, and while the plurality of elements is not between the megavoltage radiation source and the imaging device; and modify the second image based on the determined amount of scatter radiation, wherein the object to be imaged is not between the megavoltage radiation source and the imaging device during acquisition of the first image.

17. A medium storing program code, the program code comprising:

code to emit megavoltage radiation from a megavoltage radiation source;

code to acquire a first image using an imaging device while first megavoltage radiation is emitted from the megavoltage radiation source and while a plurality of elements is between the megavoltage radiation source and the imaging device, wherein an apex of each of the plurality of elements is pointed toward a focal spot of the megavoltage radiation source; and code to determine an amount of scatter radiation based at least on areas of the acquired image corresponding to the plurality of elements.

18. A medium according to claim 17, wherein the code to determine the amount of scatter radiation comprises:

code to determine, for each element, a corresponding area of the acquired image; and code to determine an amount of scatter radiation for each of the corresponding areas.

19. A medium according to claim 18, wherein the code to determine the amount of scatter radiation for each of the areas comprises:

code to determine an amount of non-scatter radiation for each of the areas, the amount of non-scatter radiation for an area comprising radiation that has passed through an element corresponding to the area.

20. A medium according to claim 17, the processing device further to:

acquire a second image while second megavoltage radiation is emitted from the megavoltage radiation source and while the plurality of elements and an object to be imaged are not between the megavoltage radiation source and the imaging device;

acquire a third image while third megavoltage radiation is emitted from the megavoltage radiation source, and while the plurality of elements and the object to be imaged are between the megavoltage radiation source and the imaging device; and acquire a fourth image while fourth megavoltage radiation is emitted from the megavoltage radiation source, while the object is between the megavoltage radiation source and the imaging device, and while the plurality of elements is not between the megavoltage radiation source and the imaging device, wherein determination of the amount of scatter radiation comprises determination, for each of the corresponding areas, of an amount of scatter radiation due to the object based on the first image, the second image, the third image, and the fourth image, wherein the object to be imaged is not between the megavoltage radiation source and the imaging device during acquisition of the first image.

21. A medium according to claim 20, the processing device further to:

modify the fourth image based on the determined amount of scatter radiation.

22. A medium according to claim 17, the processing device further to:

acquire a second image while second megavoltage radiation is emitted from the megavoltage radiation source, while an object is between the megavoltage radiation source and the imaging device, and while the plurality of elements is not between the megavoltage radiation source and the imaging device; and modify the second image based on the determined amount of scatter radiation, wherein the object to be imaged is not between the megavoltage radiation source and the imaging device during acquisition of the first image.

* * * * *